US012156804B2

(12) United States Patent
Zhang

(10) Patent No.: US 12,156,804 B2
(45) Date of Patent: Dec. 3, 2024

(54) OPTICAL DEVICES HAVING PARTIAL OR INCOMPLETE OPTIC AND ASSOCIATED METHODS

(71) Applicant: Hoya Corporation, Tokyo (JP)

(72) Inventor: Xiao Xiao Zhang, Fort Worth, TX (US)

(73) Assignee: Hoya Corporation, Tokyo (JP)

( * ) Notice: Subject to any disclaimer, the term of this patent is extended or adjusted under 35 U.S.C. 154(b) by 520 days.

(21) Appl. No.: 17/386,093

(22) Filed: Jul. 27, 2021

(65) Prior Publication Data

US 2021/0346151 A1    Nov. 11, 2021

Related U.S. Application Data

(63) Continuation of application No. 15/770,412, filed as application No. PCT/US2016/061012 on Nov. 8, 2016, now Pat. No. 11,103,344.

(60) Provisional application No. 62/252,744, filed on Nov. 9, 2015.

(51) Int. Cl.
*A61F 2/16* (2006.01)

(52) U.S. Cl.
CPC .......... *A61F 2/1648* (2013.01); *A61F 2/1602* (2013.01); *A61F 2/1654* (2013.01); *A61F 2002/1681* (2013.01); *A61F 2002/1696* (2015.04); *A61F 2002/16965* (2015.04); *A61F 2240/001* (2013.01); *A61F 2250/0053* (2013.01)

(58) Field of Classification Search
CPC .................. A61F 2/1648; A61F 2/1602; A61F 2002/1696; A61F 2250/0053; B29D 11/026
See application file for complete search history.

(56) References Cited

U.S. PATENT DOCUMENTS

| 4,451,938 A | * | 6/1984 | Kelman | ................ A61F 2/1616 623/6.19 |
| 4,596,578 A | | 6/1986 | Kelman | |
| 4,636,210 A | * | 1/1987 | Hoffer | ................... A61F 2/1616 623/6.2 |
| 4,769,033 A | * | 9/1988 | Nordan | ................. A61F 2/1618 623/6.24 |
| 5,074,876 A | | 12/1991 | Kelman | |

(Continued)

FOREIGN PATENT DOCUMENTS

| CN | 101568312 A | 10/2009 |
| EP | 1818023 B1 | 3/2009 |

(Continued)

OTHER PUBLICATIONS

International Search Report and Written Opinion dated Feb. 24, 2017 for PCT App. Ser. No. PCT/US2016/061012.

*Primary Examiner* — Javier G Blanco
(74) *Attorney, Agent, or Firm* — Henricks Slavin LLP

(57) ABSTRACT

An optical device including a partial or incomplete optic configured operatively as an add-on (e.g., supplemental lens/optic) for an (existing) optical element or system, the partial or incomplete optic having an active area configured in relation to the optical element or system such that the partial or incomplete optic controls or changes foci of light incident upon or provided to the active area, but does not control or change foci of light bypassing optically relevant portions of the partial or incomplete optic, and associated methods for enhancing vision.

13 Claims, 19 Drawing Sheets

(56) References Cited

U.S. PATENT DOCUMENTS

| | | | |
|---|---|---|---|
| 5,171,319 A * | 12/1992 | Keates | A61F 2/1664 606/107 |
| 6,129,759 A | 10/2000 | Chambers | |
| 6,280,471 B1 * | 8/2001 | Peyman | A61F 2/1613 623/6.34 |
| 7,662,179 B2 | 2/2010 | Sarfarazi | |
| 8,262,728 B2 | 9/2012 | Zhang | |
| 9,207,363 B2 | 12/2015 | Stoia et al. | |
| 11,103,344 B2 | 8/2021 | Zhang | |
| 2002/0072796 A1 | 6/2002 | Hoffmann et al. | |
| 2005/0060031 A1 | 3/2005 | Coroneo | |
| 2006/0066808 A1 | 3/2006 | Blum | |
| 2006/0259138 A1 * | 11/2006 | Peyman | A61F 2/1602 623/6.22 |
| 2012/0029631 A1 | 2/2012 | Wanders et al. | |
| 2012/0033177 A1 * | 2/2012 | Sarver | A61F 2/1602 351/159.02 |
| 2012/0259411 A1 * | 10/2012 | Hong | G02C 7/049 351/159.01 |
| 2014/0320967 A1 * | 10/2014 | Stoia | G02B 1/118 359/601 |
| 2015/0005877 A1 | 1/2015 | Wanders | |
| 2016/0220349 A1 | 8/2016 | Wanders | |
| 2018/0296324 A1 | 10/2018 | Zhang | |

FOREIGN PATENT DOCUMENTS

| | | |
|---|---|---|
| EP | 2219065 A1 | 8/2010 |
| EP | 2790052 A1 | 10/2014 |
| WO | WO 2008071760 A2 | 6/2008 |
| WO | WO 2015147758 A1 | 10/2015 |

* cited by examiner

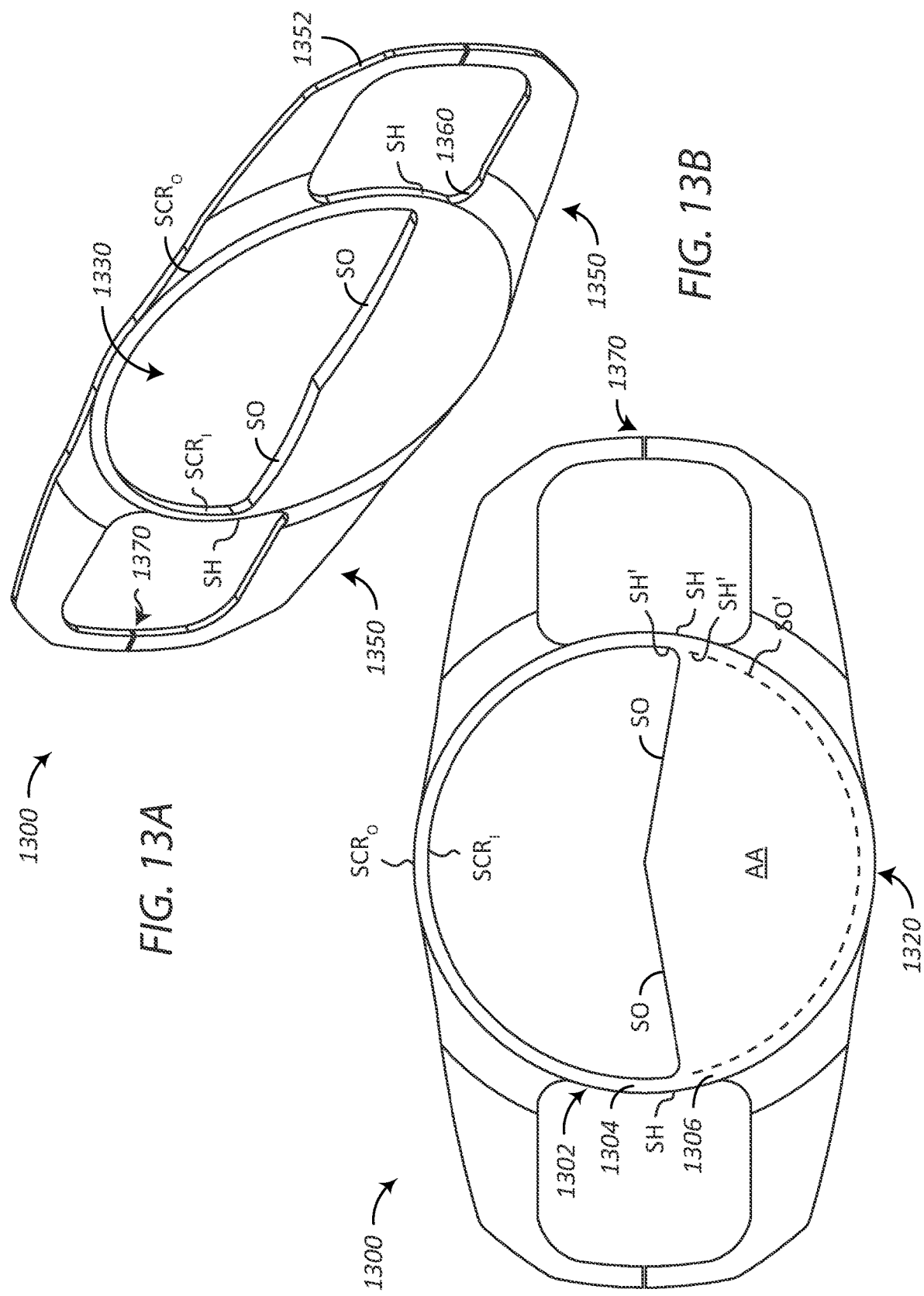

OPTICAL DEVICES HAVING PARTIAL OR INCOMPLETE OPTIC AND ASSOCIATED METHODS

CROSS-REFERENCE TO RELATED APPLICATIONS

This application a continuation of U.S. application Ser. No. 15/770,412, filed Apr. 23, 2018, now U.S. Pat. No. 11,103,344, which is the U.S. National Stage of PCT App. Ser. No. PCT/US2016/061012, filed Nov. 8, 2016, which claims the priority of U.S. provisional Application No. 62/252,744, entitled "Optical Devices Having Partial or Incomplete Optic and Associated Methods" filed on Nov. 9, 2015, the full disclosure of which is incorporated herein by reference.

TECHNICAL FIELD

The present inventions (or invention) relate(s) generally to optical devices or elements, such as a lens or optic, having designs that in operative (e.g., implanted or installed) configurations correct or improve vision obtainable by another (e.g., existing) optical element or system, and associated methods for enhancing vision.

BACKGROUND ART

FIG. 1 is a "problem formation" diagram visually depicting the formation (or etiology) of unwanted visual symptoms, halos and flare, in an example conventional circular diffractive multifocal optic, such as ReSTOR® Multifocal IOLs sold by Alcon. FIG. 8 is a pictorial representation of an eye and an optical element or system (thereof/in the eye) inclusive of the (aforementioned, with reference to FIG. 1) conventional circular diffractive multifocal optic, depicting light sweeping horizontally across the conventional circular diffractive multifocal optic and redirecting (as transient bursts) to the fovea causing flare (contributing to flare/glare). Moreover, IOLs having surface modulations defining multiple diffractive zones, such as the ReSTOR® IOL, suffer from secondary image blur due to the higher order diffractive powers.

Within the context of multifocal optics (such as, for example, LENTIS® Mplus X multifocal IOLs sold by Oculentis BV of Eerbeek, the Netherlands), prior attempts to address such problems and unwanted visual symptoms include refractive optic IOLs having a fan-shaped near vision zone that is inferiorly located which allows the patient to minimize "flare" (e.g., from moving headlights at night) by adjusting gaze upwards. Such IOLs (compared to the aforementioned diffractive multifocal optic) provide a smaller secondary blur image due to no "higher order" diffractive powers, improve resolution of intermediate objects, and reduce light scatter and perception of visual disturbances.

Many patients benefit and experience higher quality of life from optical devices such as, for example, implanted IOLs. As people age, however, vision obtainable by (with the assistance of) an existing optical device (e.g., an IOL previously implanted in the eye) changes. Moreover, the multiple different vision problems associated with aging, which typically are not simultaneous in their onset (presbyopia 45-50, cataract 60-65, advanced macular degeneration (AMD) 70-75), are often challenging to address. In some circumstances, by way of example, a previously implanted lens is difficult to remove.

It would be helpful to be able to provide an optical device in the form of an add-on (e.g., supplemental lens/optic) for an existing optical element or system (e.g., in/including an eye).

It would be helpful to be able to provide an add-on (e.g., supplemental lens/optic) for an optical element or system (e.g., that includes an optical device such as an IOL).

It would be helpful to be able to provide an optical device/add-on (e.g., supplemental lens/optic) for an existing optical element or system (e.g., in/including an eye) that corrects or improves a specific aspect (or area) of vision obtainable by the existing optical element or system (e.g., addresses only a new or subsequently developing/presenting vision problem without effecting other vision that the existing optical element or system obtains).

It would be helpful to be able to provide an optical device (e.g., supplemental lens/optic) that reduces unwanted visual symptoms, halos and flare, and/or perception of visual disturbances.

SUMMARY OF THE INVENTION

Embodiments described herein relate to technologies and methodologies for providing an optical device including, or in the form of, a partial or incomplete optic configured operatively as an add-on (e.g., supplemental lens/optic) for an (existing, as in already built/constructed/assembled, or already or previously installed) optical element or system. The partial or incomplete optic is provided, for example, as an add-on lens/optic for another lens (e.g., that was previously implanted) in the eye. In example embodiments and implementations, the partial or incomplete optic is configured to address, or is directed primarily or solely to, a vision problem that developed or presented subsequent to an implantation and/or other positioning of an optical element or system previously (and, in some instances, still) existing in the eye. In example embodiments and implementations, the partial or incomplete optic is configured to address, or is directed primarily or solely to, a second (e.g., untreated or inadequately treated) vision problem that was already co-existing with a first vision problem that an optical element or system was previously provided to address. In example embodiments and implementations, the partial or incomplete optic and another optical element or system are configured to address multiple vision problems. For example, an optical element or system (e.g., a first lens) directed to a first vision problem and a partial or incomplete optic (e.g., a partial optic/lens) directed to a second vision problem can be configured/implanted together (e.g., during the course of one surgery or a single invasive procedure), or the partial or incomplete optic can be configured/implanted shortly after the optical element or system is configured/implanted (or vice versa). The partial or incomplete optic can be provided, by way of example, as an add-on lens/optic (e.g., in the form of an IOL and/or partial disc) having or effectively providing an active area (or portion(s), e.g., one or more regions or sectors) that magnifies images by creating a near focal point, e.g., by adding a single power or a multifocal (sector) optic to an (existing) optical element or system.

In an example embodiment, an optical device includes: a partial or incomplete optic configured operatively as an add-on (e.g., supplemental lens/optic) for an (existing) optical element or system, the partial or incomplete optic having an active area (or portion(s), e.g., one or more regions or sectors) configured in relation to the optical element or system such that the partial or incomplete optic controls or changes foci of light incident upon or provided to the active area, but does not control or change foci of light bypassing optically relevant portions of the partial or incomplete optic.

In example embodiments and implementations, the active area (e.g., a fan-shaped sector) of the partial or incomplete optic is configured (e.g., in relation to the optical element or system) such that a line of sight (LOS) or a visual axis (VA) of or associated with the (existing) optical element or system is at or near (intersects) a top portion of the active area (of the partial or incomplete optic).

In example embodiments and implementations, the active area (of the partial or incomplete optic) includes or is provided with (one or more) edge or side portions (e.g., including generally radially directed transitions/zones) configured and/or treated to effect blocking (occlusion) or diffusion of light (i.e., stray light, specifically, transient bursts occurring as light sweeps horizontally across the edge or side portions of the optical device, that otherwise could redirect into the fovea contributing to flare/glare). For example, the edge or side portions can include (or be provided with): a light absorbing surface layer, a surface treatment or finish, nano-structures (e.g., that have nano-tips or cones), or a combination or combinations of such light effecting structures.

In an example embodiment, a method for enhancing vision includes: providing a partial or incomplete optic as an add-on to an existing optical element or system, the partial or incomplete optic having an active area (or portion(s), e.g., one or more regions or sectors) configured in relation to the existing optical element or system such that the partial or incomplete optic controls or changes foci of light incident upon or provided to the active area, but does not control or change foci of light bypassing optically relevant portions of the partial or incomplete optic.

In example embodiments and implementations, the partial or incomplete optic is positioned (in relation to the existing optical element or system) such that the active area (of the partial or incomplete optic) controls or changes foci of light incident upon or provided to the existing optical element or system at an optical region (or area) thereof. In example embodiments and implementations, this optical region (or area) of the existing optical element or system is (generally) fan-shaped and/or at least partially (e.g., mostly) below (below, in elevational sense) a line of sight (LOS) or a visual axis (VA) of or associated with the existing optical element or system.

In example embodiments and implementations, the existing optical element or system includes a lens (or other optic) implanted in an eye (e.g., a human eye) (or other seeing mechanism or device), and the step of providing a partial or incomplete optic is performed subsequent to the lens (or other optic) being implanted.

The method for enhancing vision can further include providing the active area (of the partial or incomplete optic) with (one or more) edge or side portions that block (occlude) or diffuse light (i.e., stray light, specifically, transient bursts occurring as light sweeps horizontally across the edge or side portions, that otherwise could redirect into the fovea contributing to flare/glare). For example, process(es) facilitating or utilized in providing edge or side portions that block (occlude) or diffuse light can include: applying a surface treatment or finish (e.g., a matte finish) at the edge or side portions from outside-in without affecting optical areas; applying a light absorbing surface layer at the edge or side portions; applying a surface (roughness/modification) treatment at the edge or side portions; applying a surface finish (imparting surface roughness within a range of peak-valley height values) at the edge or side portions; utilizing a lithography or etching technique to apply and/or modify one or more surface structures at the edge or side portions; providing nano-structures, e.g., nano-tips (cones), at the edge or side portions; or a combination or combinations of such processes.

BRIEF DESCRIPTION OF THE DRAWINGS

FIGS. 13A and 13B are perspective and plan views, respectively, of an example embodiment of an optical device including a partial or incomplete optic, such as or similar to that of FIGS. 2A and 2B, and a circumferential ring and haptics configured to be iris-fixated (the optical device and its partial or incomplete optic, in various implementations, being of and embodying a lens/optic design that is configurable operatively to serve as or provide an add-on to an existing optical element or system);

DISCLOSURE OF INVENTION

Example embodiments of the invention(s) described herein involve optical devices including, or in the form of, a partial or incomplete optic configured operatively as an add-on or supplemental lens/optic (e.g., in the form of an IOL and/or partial disc) for another optical element or system (e.g., a lens previously implanted in an eye). It is contemplated that the principles of the present invention(s) are applicable to lens/optic element(s) for and may be appropriately adapted in various implementations to other optical devices including but not limited to contact lenses.

Figure 2A:
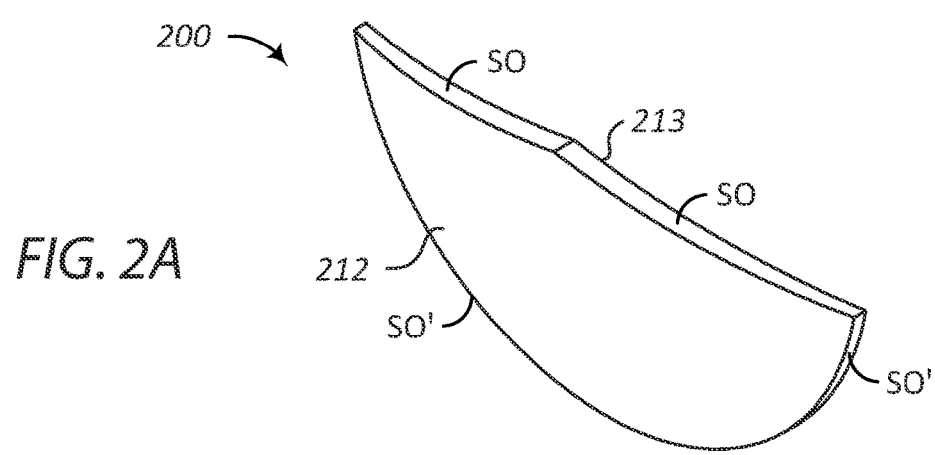
FIGS. 2A and 2B are perspective and plan views, respectively, of an example embodiment of a partial or incomplete optic (which, in various implementations, provides or is part of an optical device and/or is of a lens/optic design that is configurable operatively to serve as or provide an add-on to an existing optical element or system)
Figure 2B:
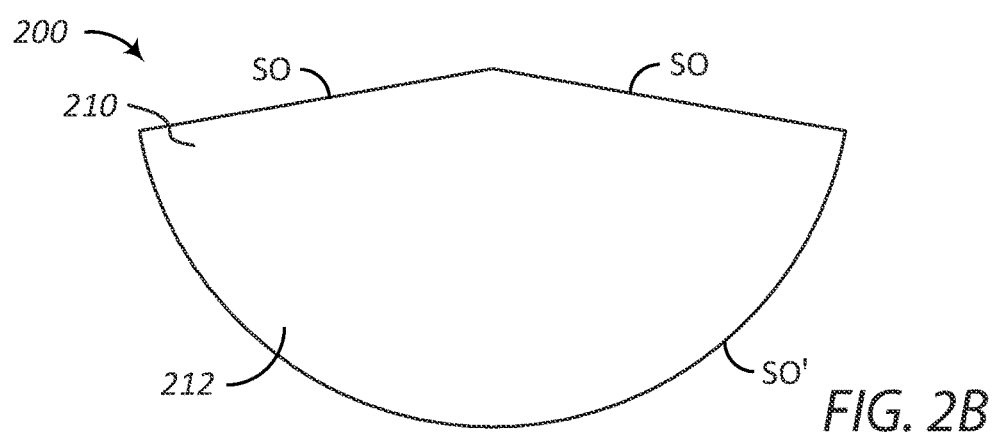

FIGS. 2A and 2B show an example embodiment of a partial or incomplete optic 200. In various implementations, a partial or incomplete optic (e.g., such as described herein) provides or is part of an optical device and/or is of a lens/optic design that is configurable operatively to serve as or provide an add-on to an existing optical element or system.

Figure 3:
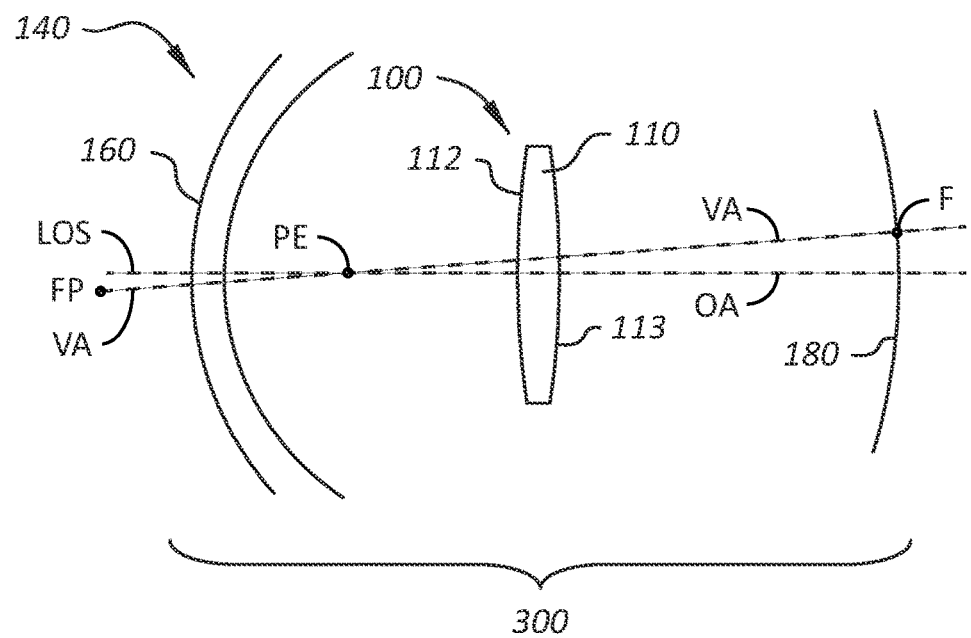
FIG. 3 is a schematic view showing an example of an (existing) optical element or system in an eye.

FIG. 3 shows an optical element or system 300 that includes an optical device or optic 100 (such as for example an IOL). The optical element or system 300 also includes, or can be considered to include, an eye 140 with a cornea 160 and retina 180, and as to which the fovea is denoted "F" and the pupil entrance is denoted "PE". Haptics (not shown in this figure) may also be provided. The (existing) optical device or optic 100 includes a lens body 110 having an anterior lens surface (or portion) 112 and a posterior lens surface (or portion) 113.

Figure 4A:
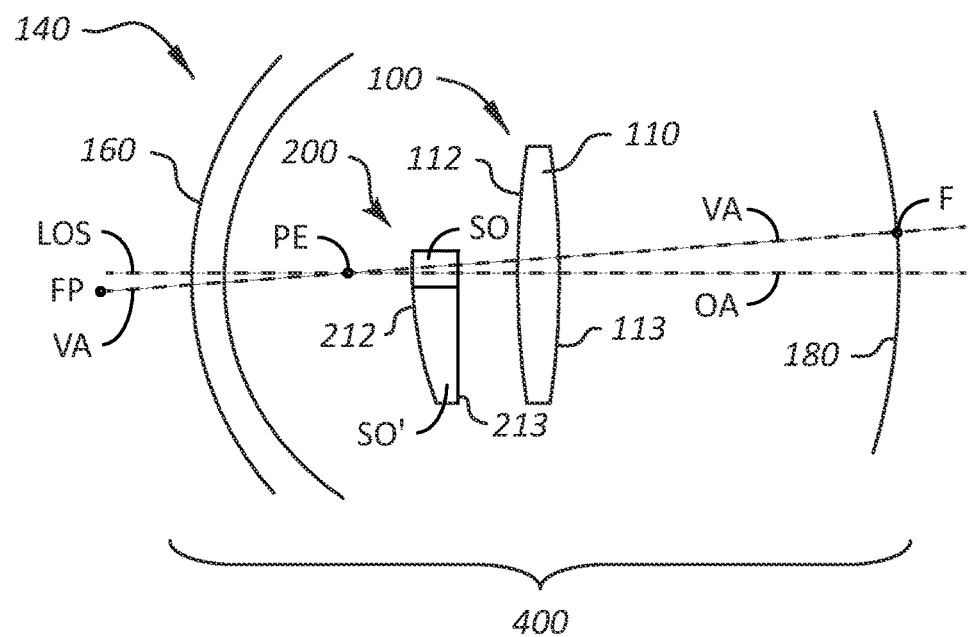
FIG. 4A is a schematic view showing an optical element or system in (/including) an eye, the optical element or system including an optical device or optic (e.g., in the form of an IOL) and a partial or incomplete optic, such as or similar to that of FIGS. 2A and 2B, configured operatively, and located partially above a line of sight (LOS) or a visual axis (VA) of or associated with the optical element or system, as an add-on to the optical element or system in accordance with at least one embodiment of a present invention.

Example embodiments and implementations of the technologies and methodologies described herein involve an optical element or system (e.g., including an IOL and/or other optical device) that includes or is provided with a partial or incomplete optic (e.g., such as or similar to the partial or incomplete optic 200 of FIGS. 2A and 2B). FIG. 4A shows an example embodiment of an optical element or system 400 in (/including) an eye. Example embodiments and implementations involve an optical device that includes (or consists of) a partial or incomplete optic, such as or similar to the partial or incomplete optic 200 of FIGS. 2A and 2B. The optical element or system 400 includes optical device or optic 100 (such as for example an IOL) and a partial or incomplete optic 200 configured operatively as an add-on to the optical element or system. Referring also to FIGS. 2A, 2B, the partial or incomplete optic 200 includes a lens body 210 having an anterior lens surface (or portion) 212 and a posterior lens surface (or portion) 213. The anterior lens surface (or portion) 212 can be spherical or, alternatively or in addition, aspheric, and/or multifocal, and the posterior lens surface (or portion) 213 can be planar, spherical or, alternatively or in addition, aspheric, or toric, or vice versa.

Suitable material for a partial or incomplete optic (e.g., in the form of an IOL) includes, but is not limited to, HOYA material A, which is a hydrophobic acrylic material (U.S. Pat. No. 7,714,090) and the discussion herein (where appropriate) assumes the use of this material. Other suitable materials include, but are not limited to, PMMA and other silicone or acrylic materials, which are appropriate for an IOL and/or other optics. In other example embodiments and implementations, a hydrophilic material is utilized.

Figure 4B:
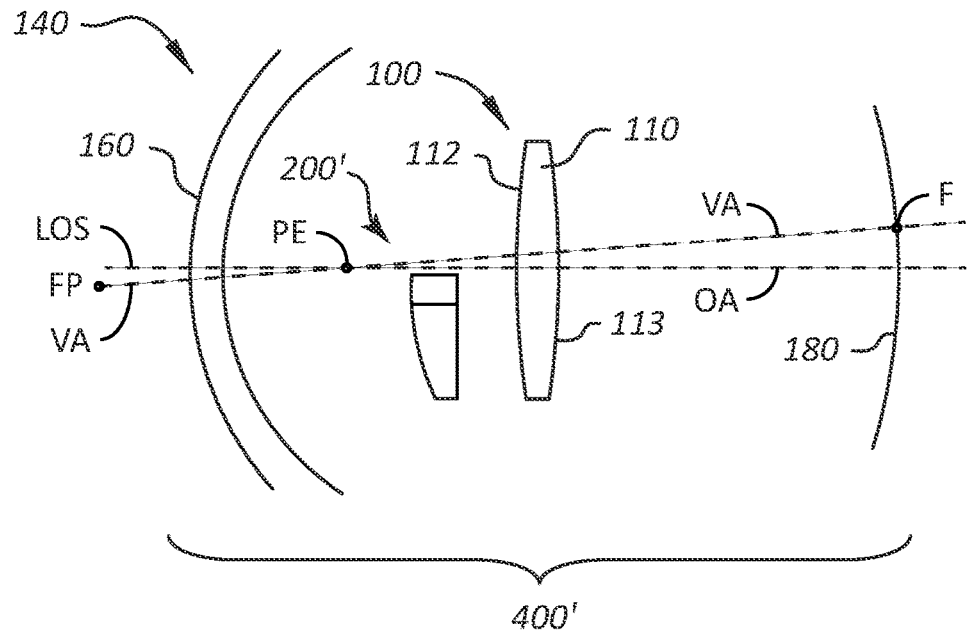
FIG. 4B is a schematic view showing an optical element or system in (/including) an eye, the optical element or system including an optical device or optic (e.g., in the form of an IOL) and a partial or incomplete optic, such as or similar to that of FIGS. 2A and 2B, configured operatively, and located below or inferiorly in relation to a line of sight (LOS) or a visual axis (VA) associated with the optical element or system, as an add-on to the optical element or system in accordance with at least one embodiment of a present invention.

The partial or incomplete optic 200 includes or is provided with edge or side portions, e.g., two symmetrical surfaces (each denoted "SO") and an adjoining curved surface (denoted "SO'"). As further discussed below (with reference to FIGS. 15A and 15B), in example embodiments, an (optical) active area of the partial or incomplete optic 200 has a (peripheral) boundary which, at least in part, includes or is defined by one or more edge or side portions/surfaces of the lens body 210 (such as for example the surfaces SO, SO'). In the example embodiment depicted in FIG. 4A, the partial or incomplete optic 200 is located partially above (e.g., but mostly below, or inferiorly in relation to) a line of sight (LOS), and/or a visual axis (VA), of or associated with the optical element or system 400. With reference to FIG. 4B, in another example embodiment, a partial or incomplete optic 200' (e.g., such as or similar to the partial or incomplete optic 200) is configured operatively as an add-on to the optical element or system 400', and located below or inferiorly in relation to a line of sight (LOS), and/or a visual axis (VA), associated with the optical element or system.

Figure 5:
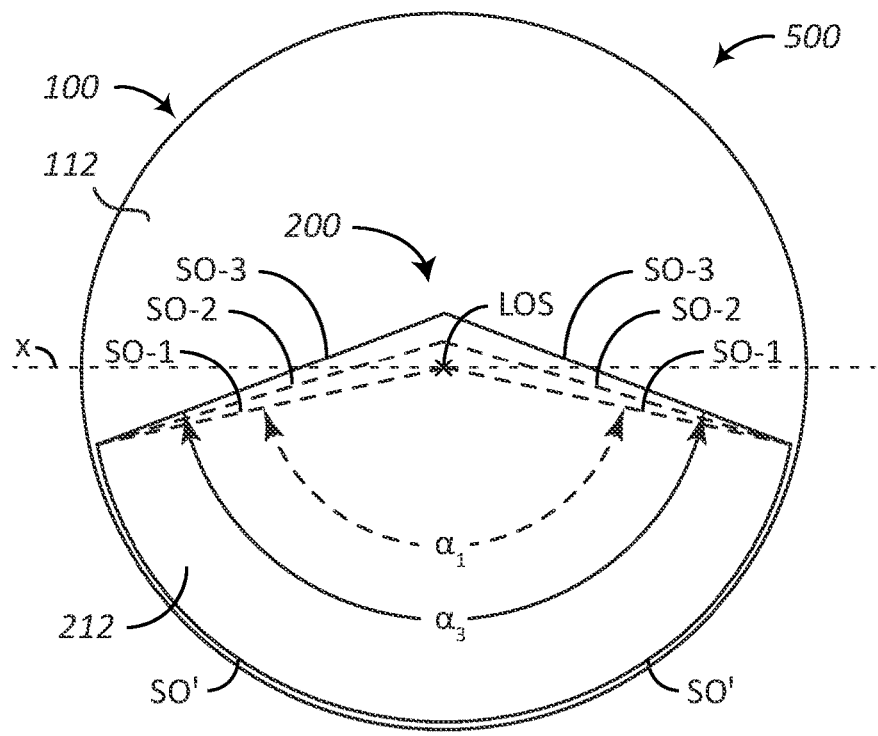
FIG. 5 is a plan view showing an optical element or system (e.g., in the form of an IOL) and a partial or incomplete optic, such as or similar to that of FIGS. 2A, 2B and 4A, configured operatively, and located partially above (e.g., but mostly below, or inferiorly in relation to) a line of sight (LOS) or a visual axis (VA) of or associated with the existing optical element or system, as an add-on to the optical element or system in accordance with at least one embodiment of a present invention.

FIG. 5 shows an optical element or system 500 (e.g., in the form of an IOL) and partial or incomplete optic 200 configured operatively as an add-on to the optical element or system. In example embodiments and implementations, an active area of the partial or incomplete optic has a shape (e.g., including boundary portions/surfaces of the optic) in relation to which its active area can be described as having an angular width α. For example, as shown in FIG. 5, an active area of the partial or incomplete optic 200 includes or is provided with a symmetrical pair of edge or side surfaces (denoted "SO-3") in relation to which an angular width (denoted "$α_3$") of the partial or incomplete optic is defined or otherwise established. Partial or incomplete optics can have various shapes inclusive of lens body designs with symmetrical portions/surfaces. For example, and referring again to FIG. 5, pairs of generally radially directed boundary portions/surfaces (denoted "SO-1" and "SO-2", shown in dashed lines) can alternatively be provided.

Partial or incomplete optics can be located (positioned) and configured in various ways in relation to an optical element or system, e.g., that includes (or consists of) optical device or optic 100 (such as for example an IOL). With reference to FIG. 4A, in this example embodiment, the partial or incomplete optic 200 is located partially above (e.g., but mostly below, or inferiorly in relation to) a line of sight (LOS), and/or a visual axis (VA), of or associated with the optical element or system 400. With reference to FIG. 4B, in this example embodiment, the partial or incomplete optic 200' is located below or inferiorly in relation to a line of sight (LOS), and/or a visual axis (VA), of or associated with the optical element or system 400'.

Figure 1:
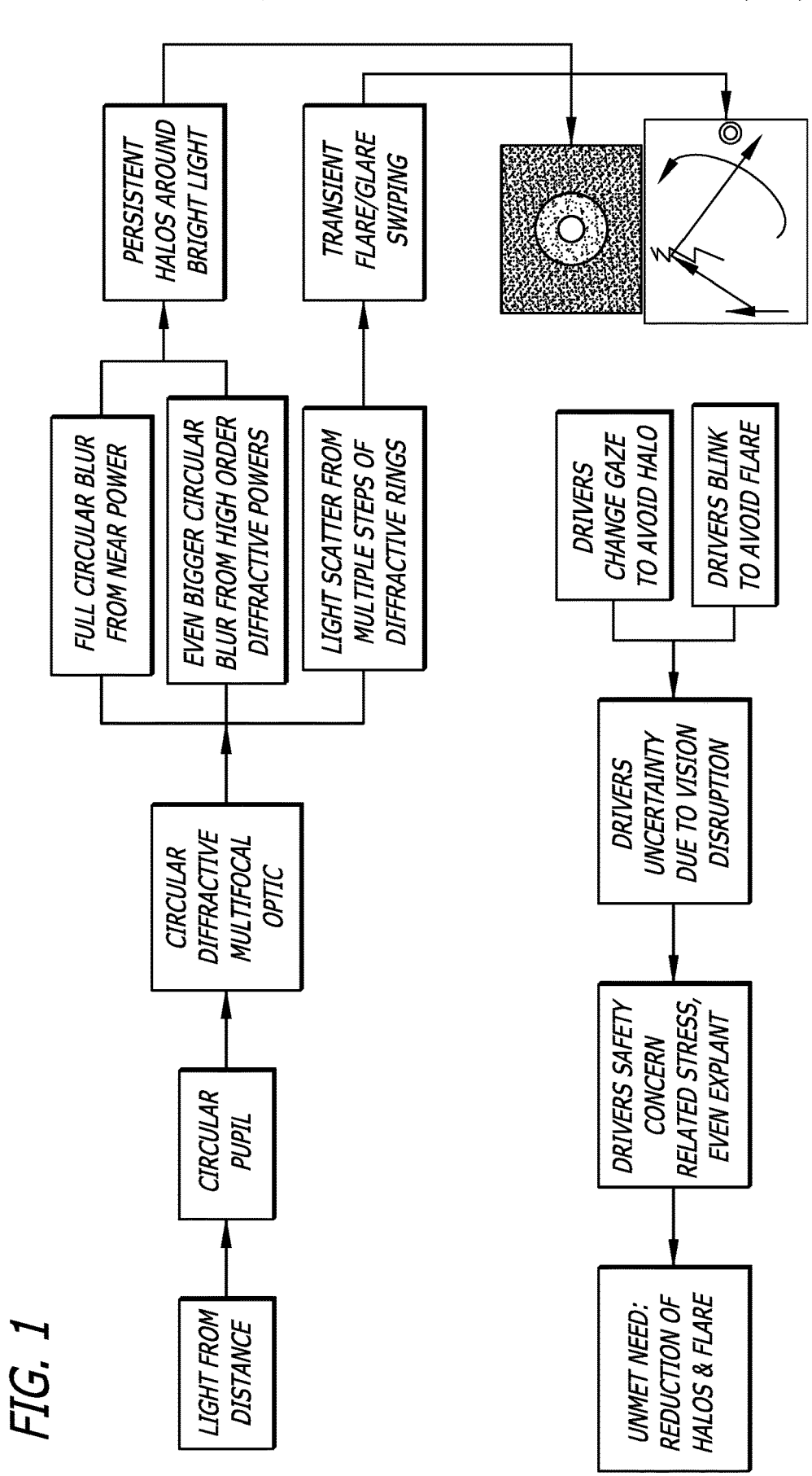
FIG. 1 is a "problem formation" diagram visually depicting the formation (or etiology) of unwanted visual symptoms, halos and flare, in an example conventional circular diffractive multifocal optic.
Figure 6:
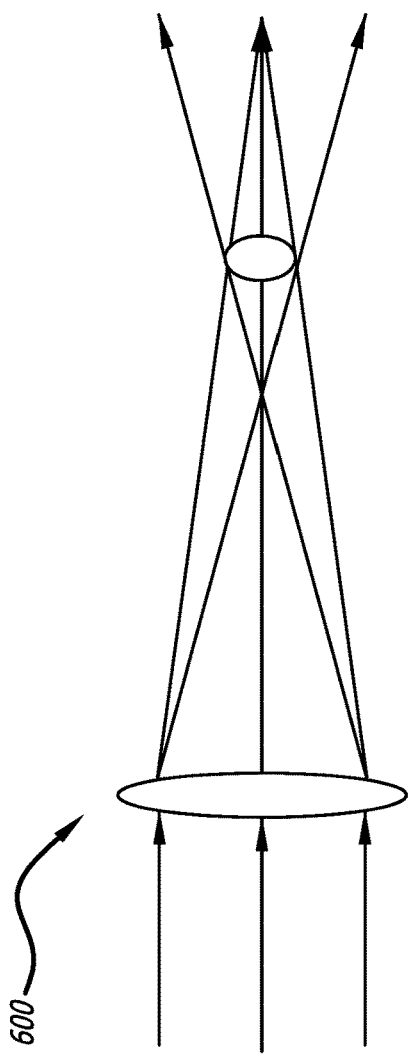
FIG. 6 illustrates how the (aforementioned, with reference to FIG. 1) conventional circular diffractive multifocal optic receives and redirects light (from distance) providing two full circle blur disks (far plus near powers) that form the waist of the light beam as shown, which results in lower optical resolution in intermediate vision.

FIG. 6 illustrates how a conventional circular diffractive multifocal optic 600 (such as previously discussed with reference to FIG. 1) receives and redirects light (from distance) providing two full circle blur disks (far plus near powers) that form the waist of the light beam as shown, which results in lower optical resolution in intermediate vision as compared with that provided by a monofocal optic (for example, 20/60 Visual Acuity in intermediate vision as compared with 20/20 Visual Acuity for far vision).

Figure 7:
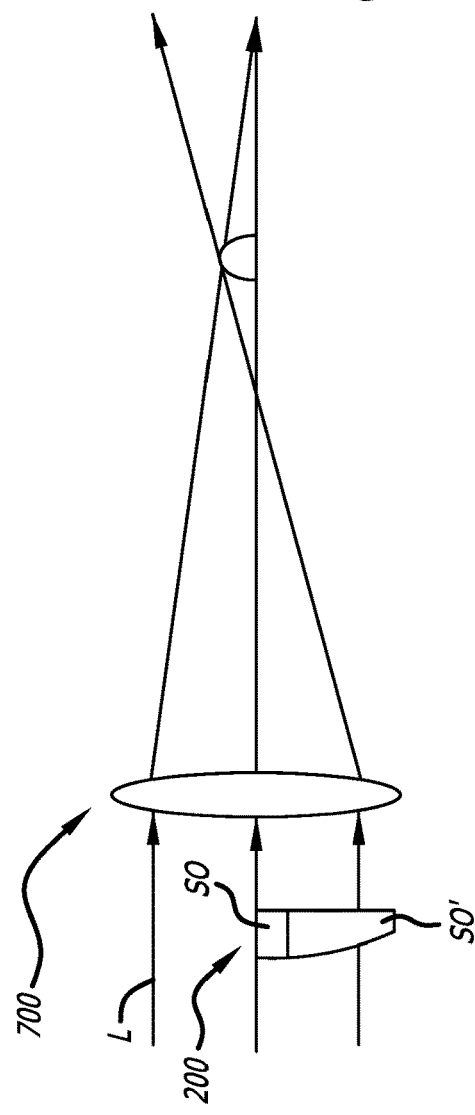
FIG. 7 illustrates how an existing refractive (or other) optic, together with a partial or incomplete optic (e.g., such as or similar to that of FIGS. 2A and 2B) configured operatively as an add-on that magnifies images by creating a near focal point, receives and redirects light (from distance) providing two half circle blur disks (far plus near powers) that form a smaller waist of the light beam (compared to that provided by the conventional circular diffractive multifocal optic as shown in FIG. 6), which provides improved optical resolution in intermediate vision.
Figure 8:
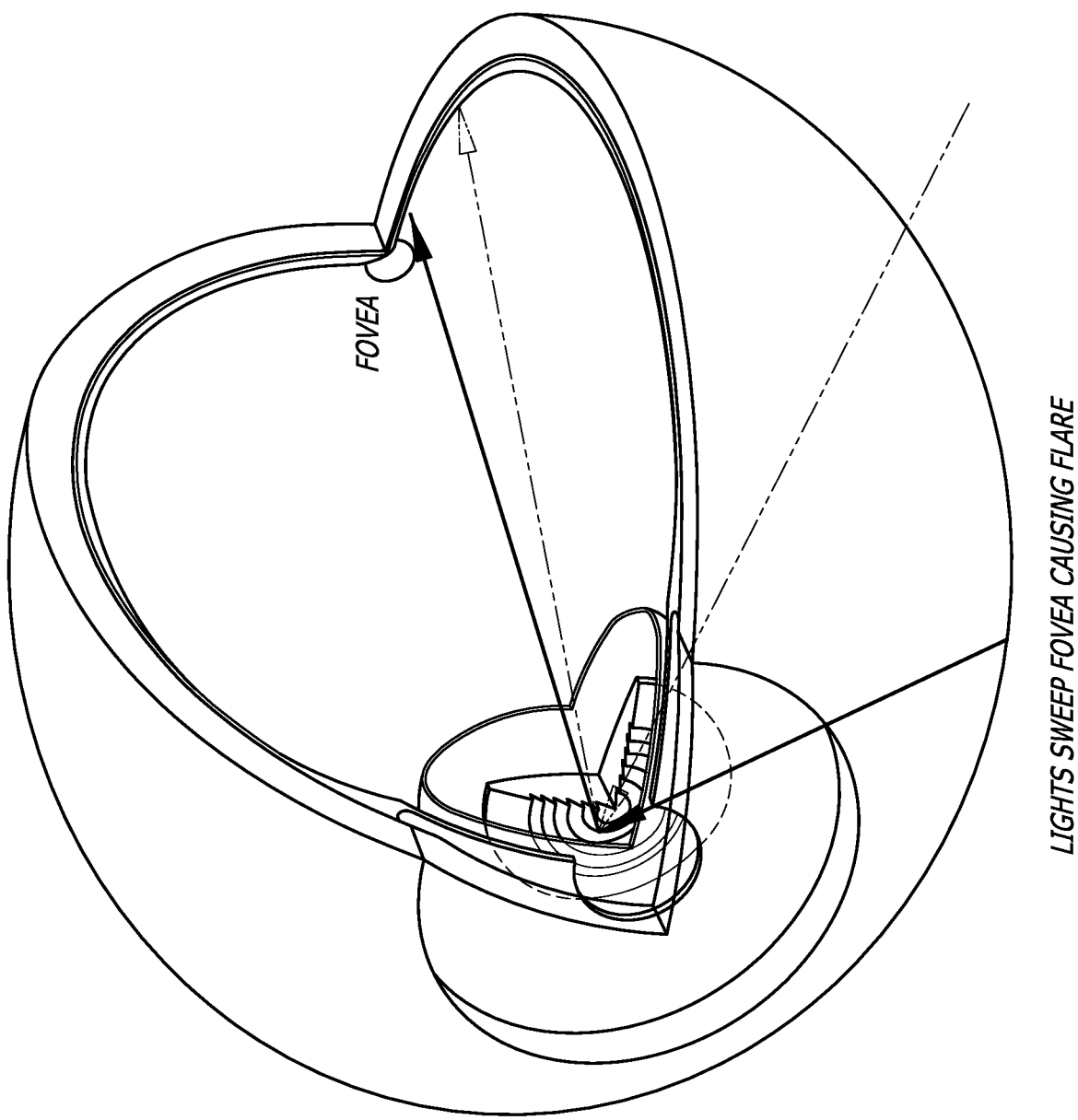
FIG. 8 is a perspective partially cross-sectional pictorial representation of an eye and an optical element or system (thereof/in the eye) inclusive of the conventional circular diffractive multifocal optic (aforementioned, with reference to FIG. 1), the illustration depicting light sweeping horizontally across the conventional circular diffractive multifocal optic and redirecting (as transient bursts) to the fovea causing flare (contributing to flare/glare)

FIG. 7 illustrates how an existing (refractive, diffractive, or other) optic 700, together with a partial or incomplete optic 200 configured operatively as an add-on that magnifies images by creating a near focal point, receives and redirects light (from distance) providing two half circle blur disks (far plus near powers) that form a smaller waist of the light beam (compared to that provided by the conventional circular diffractive multifocal optic as shown in FIG. 6), which provides improved optical resolution in intermediate vision by about a factor of 2 (for example, from 20/60 Visual Acuity in FIG. 6 to 20/30 Visual Acuity in FIG. 7 for certain visual tasks such as resolving a line stripe pattern). By way of example, a partial or incomplete optic 200 can configured with an existing diffractive optic (e.g., such as previously discussed with reference to FIG. 1) to shift the bifocal foci from the effected bottom optic relative to the top unaffected bifocal foci, to form 3 foci or 4 foci.

Partial or incomplete optics such as described herein (e.g., such as or similar to that of FIGS. 2A and 2B) can be configured operatively as add-on/supplemental optics to (existing/other) optical elements or systems including, but not limited to, for example: for a pseudo-phakic eye having a monofocal IOL of 21 D optical power, adding an add-on/supplement optic of 3.0 D optical power which provides the eye a bifocal vision of 21 D distance power and 24 D near power to serve/aid the presbyopia need of the patient; for an AMD (or low vision) eye having a monofocal IOL of 21 D optical power, adding an add-on/supplement optic of 10.0 D optical power which provides the eye a bifocal vision of 21 D distance power and 31 D near power to serve the close/near activity needs of the patient. Partial or incomplete optics such as described herein can be configured operatively as add-on/supplemental optics (e.g., as shown in FIG. 4A or FIG. 4B) to an (existing/other) optical element or system that includes (or consists of) a refractive (or other) optic. Partial or incomplete optics such as described herein can be configured operatively as add-on/supplemental optics (e.g., as shown in FIG. 5 or FIG. 7) to (existing/other) optical elements or systems that include, or can be considered to include, an eye.

For a partial or incomplete optic 200 that magnifies images by creating a near focal point, whether configured (operatively as an add-on/supplemental optic to the optic 700) in a manner such as shown in FIG. 4A, or as shown in FIG. 4B, in either case, such an optic 200 receives and redirects light (from distance) providing two half circle blur disks (far plus near powers) that form a smaller waist of the light beam (as previously discussed in relation to FIG. 7).

Figure 9:
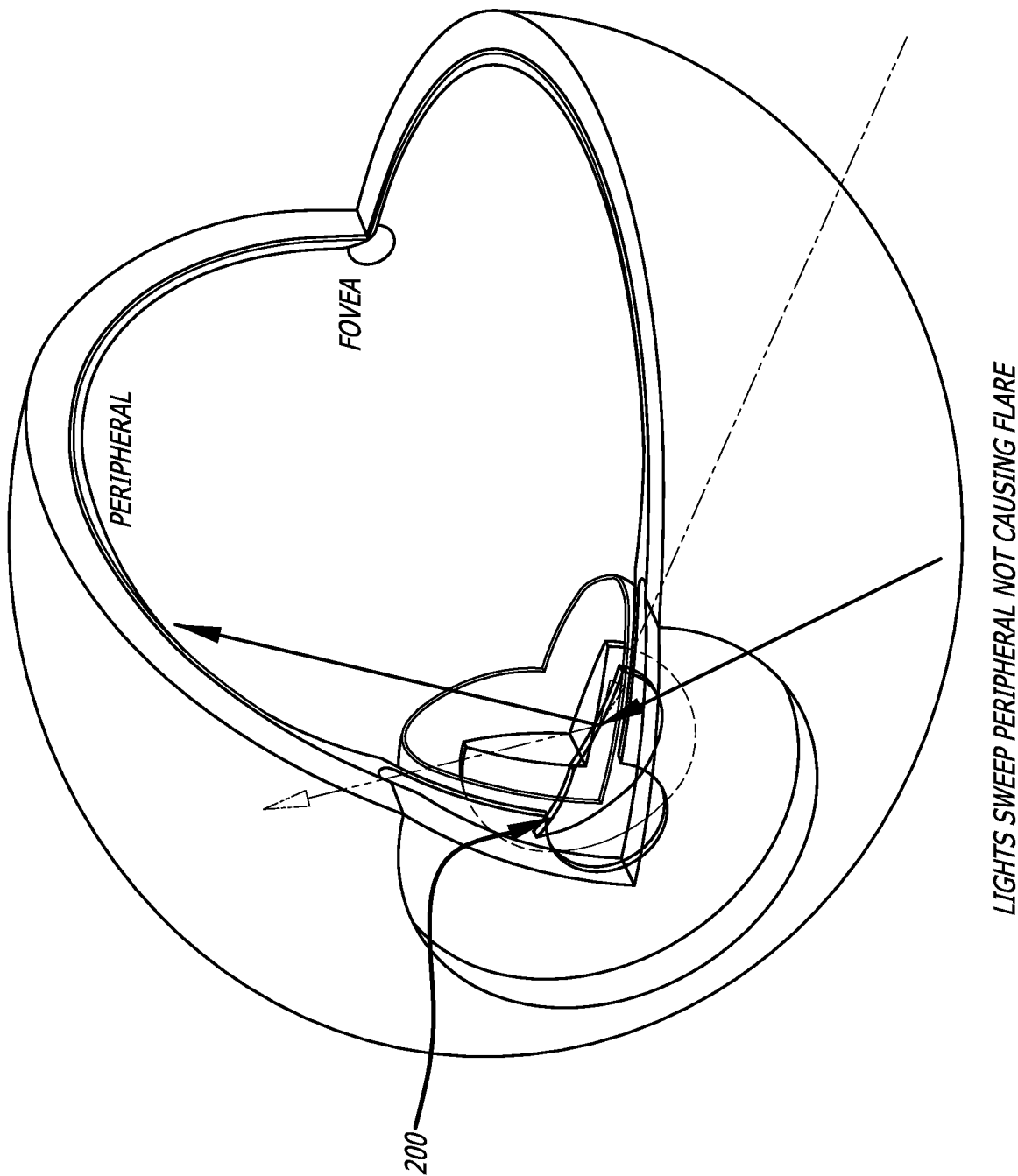
FIG. 9 is a perspective partially cross-sectional pictorial representation of an eye and a partial or incomplete optic, such as or similar to that of FIGS. 2A and 2B, configured operatively as an add-on to an optical element or system (e.g., an IOL, previously implanted, with the upper right quadrant removed for better illustration purpose) in the eye, the illustration depicting light sweeping horizontally across the partial or incomplete optic and redirecting (as shown) peripheral to the fovea not causing flare.

For a partial or incomplete optic 200, such as or similar to that of FIGS. 2A and 2B, configured operatively as an add-on/supplemental optic to an (existing/other) optical element or system (e.g., an IOL) in a manner such as shown in FIG. 4A, or as shown in FIG. 5, in either case, such an optic 200 receives light sweeping horizontally across the partial or incomplete optic and redirects the light (as shown in FIG. 9) peripheral to the fovea not causing flare.

Referring again to FIG. 7, for a partial or incomplete optic 200 configured operatively as an add-on/supplemental optic to an (existing/other) optical element or system that includes (or consists of) the optic 700 (e.g., an IOL) (e.g., in a manner such as shown in one or more of FIGS. 4A, 4B, 5 and 7), the partial or incomplete optic has an active area (or portion(s), e.g., one or more regions or sectors) configured in relation to the optic 700 such that the partial or incomplete optic controls or changes foci of light incident upon or provided to the active area, but does not control or change foci of light (denoted "L" in FIG. 7) bypassing optically relevant portions of the partial or incomplete optic.

Example embodiments and implementations involve an optical device having a partial or incomplete optic (e.g., such as described herein) that also includes or is provided with one or more clip, claw, anchor, haptic or support structure.

Figure 10A:
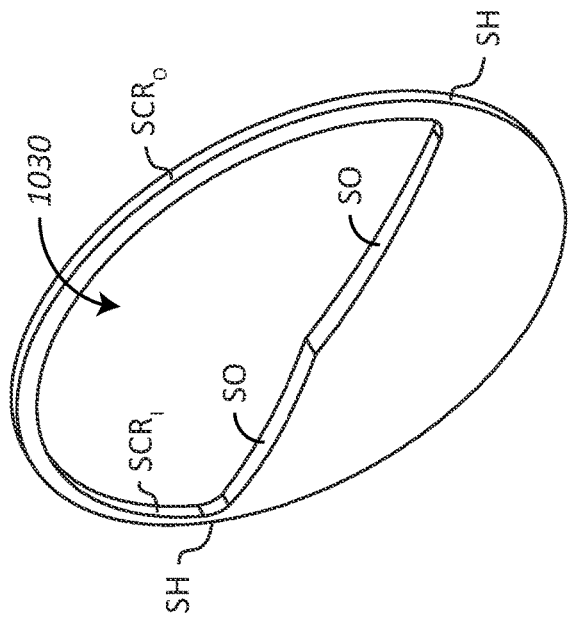
FIGS. 10A and 10B are perspective and plan views, respectively, of an example embodiment of an optical device including a partial or incomplete optic, such as or similar to that of FIGS. 2A and 2B, and a circumferential ring (the optical device and its partial or incomplete optic, in various implementations, being of and embodying a lens/optic design that is configurable operatively to serve as or provide an add-on to an existing optical element or system)
Figure 10B:
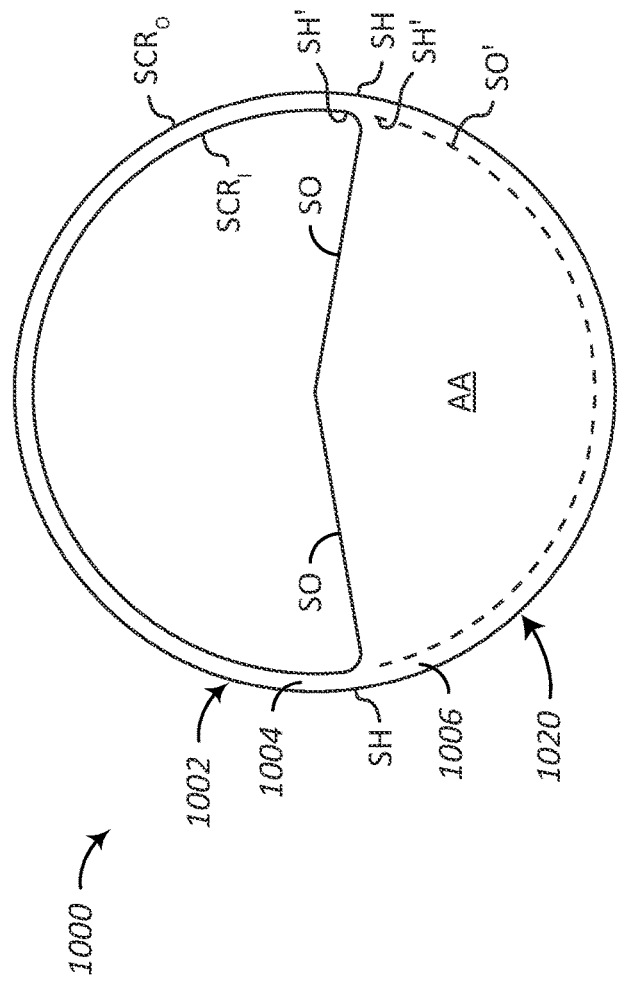

FIGS. 10A and 10B show an example embodiment of an optical device 1000 including a partial or incomplete optic 1020, such as or similar to the partial or incomplete optic 200 of FIGS. 2A and 2B, and a circumferential ring 1002 (the optical device 1000 and its partial or incomplete optic 1020, in various implementations, being of and embodying a lens/optic design that is configurable operatively to serve as or provide an add-on to an existing optical element or system). The circumferential ring 1002 includes an upper ring portion 1004 and a lower ring (/optic support) portion 1006 (e.g., shaped/configured as shown). The upper ring portion 1004 includes an inner surface (denoted "$SCR_I$") and an outer surface (denoted "$SCR_O$"). The partial or incomplete optic 1020 includes or is provided with edge or side portions, e.g., two symmetrical surfaces (each denoted "SO") and an adjoining curved surface (denoted "SO'", and shown in dashed lines). In at least one example embodiment, an (optical) active area (denoted "AA") (or an optically relevant portion) of the partial or incomplete optic 1020 has a (peripheral) boundary which, at least in part, includes or is defined by one or more edge or side portions/surfaces of the optic 1020 (such as for example the surfaces SO, SO'). The inner surface $SCR_I$ (of the upper ring portion 1004) together with the edge or side portion(s)/surface(s) SO (of the partial or incomplete optic 1020) define an opening 1030 (or an effectively optically irrelevant portion) of the partial or incomplete optic 1020.

Figures 11A, 11B:
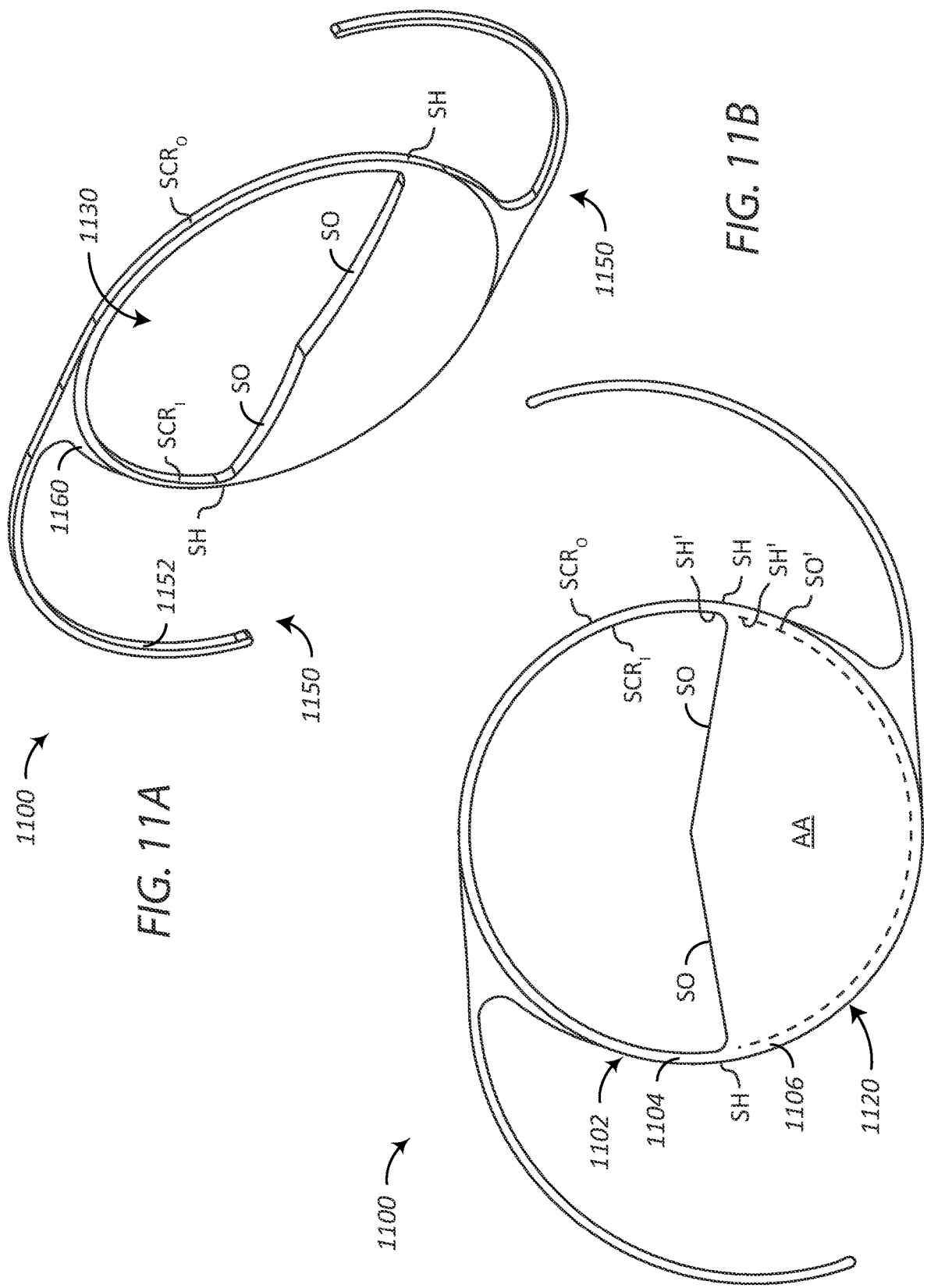
FIGS. 11A and 11B are perspective and plan views, respectively, of an example embodiment of an optical device including a partial or incomplete optic, such as or similar to that of FIGS. 2A and 2B, and a circumferential ring and loop haptics (the optical device and its partial or incomplete optic, in various implementations, being of and embodying a lens/optic design that is configurable operatively to serve as or provide an add-on to an existing optical element or system)

FIGS. 11A and 11B show an example embodiment of an optical device 1100 including a partial or incomplete optic 1120, such as or similar to the partial or incomplete optic 200 of FIGS. 2A and 2B, and a circumferential ring 1102 and loop haptics 1150 (the optical device 1100 and its partial or incomplete optic 1120, in various implementations, being of and embodying a lens/optic design that is configurable operatively to serve as or provide an add-on to an existing optical element or system). The circumferential ring 1102 includes an upper ring portion 1104 and a lower ring (/optic support) portion 1106 (e.g., shaped/configured as shown). The loop haptics 1150 include, at opposing exterior portions of the ring 1102, arms 1152 and base/interconnect elements 1160 (e.g., shaped/configured as shown). The upper ring portion 1104 includes an inner surface (denoted "$SCR_I$") and an outer surface (denoted "$SCR_O$"). The partial or incomplete optic 1120 includes or is provided with edge or side portions, e.g., two symmetrical surfaces (each denoted "SO") and an adjoining curved surface (denoted "SO'", and shown in dashed lines). In at least one example embodiment, an (optical) active area (denoted "AA") (or an optically relevant portion) of the partial or incomplete optic 1120 has a (peripheral) boundary which, at least in part, includes or is defined by one or more edge or side portions/surfaces of the optic 1120 (such as for example the surfaces SO, SO'). The inner surface $SCR_I$ (of the upper ring portion 1104) together with the edge or side portion(s)/surface(s) SO (of the partial or incomplete optic 1120) define an opening 1130 (or an effectively optically irrelevant portion) of the partial or incomplete optic 1120.

Figure 12A:
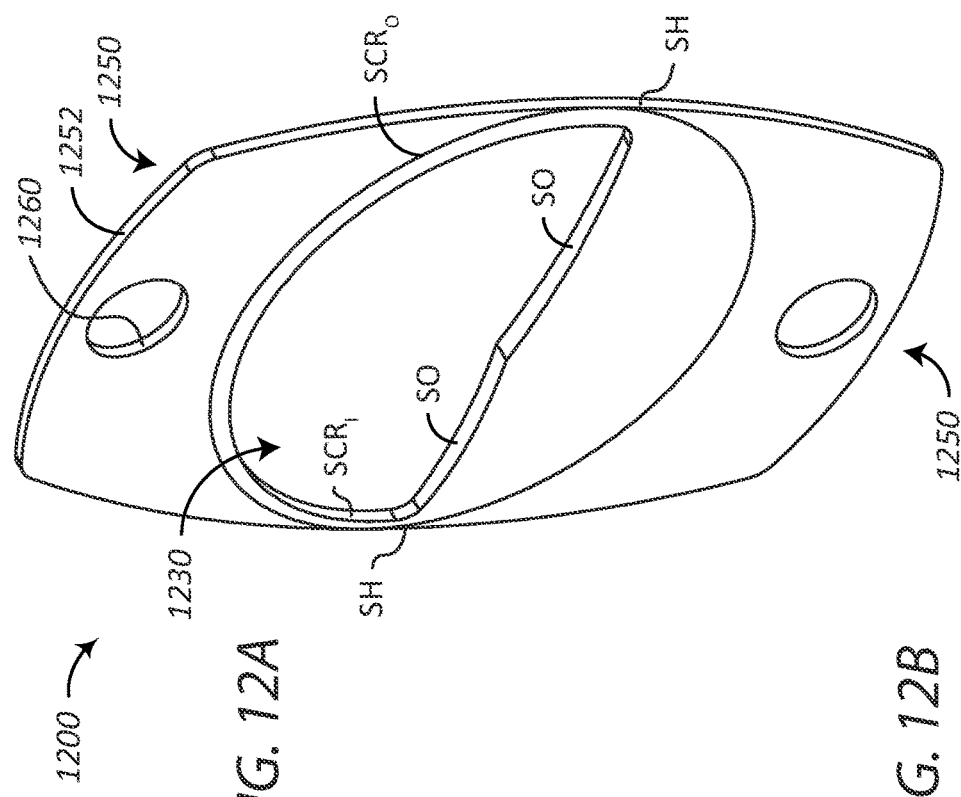
FIGS. 12A and 12B are perspective and plan views, respectively, of an example embodiment of an optical device including a partial or incomplete optic, such as or similar to that of FIGS. 2A and 2B, and a circumferential ring and plate haptics (the optical device and its partial or incomplete optic, in various implementations, being of and embodying a lens/optic design that is configurable operatively to serve as or provide an add-on to an existing optical element or system)
Figure 12B:
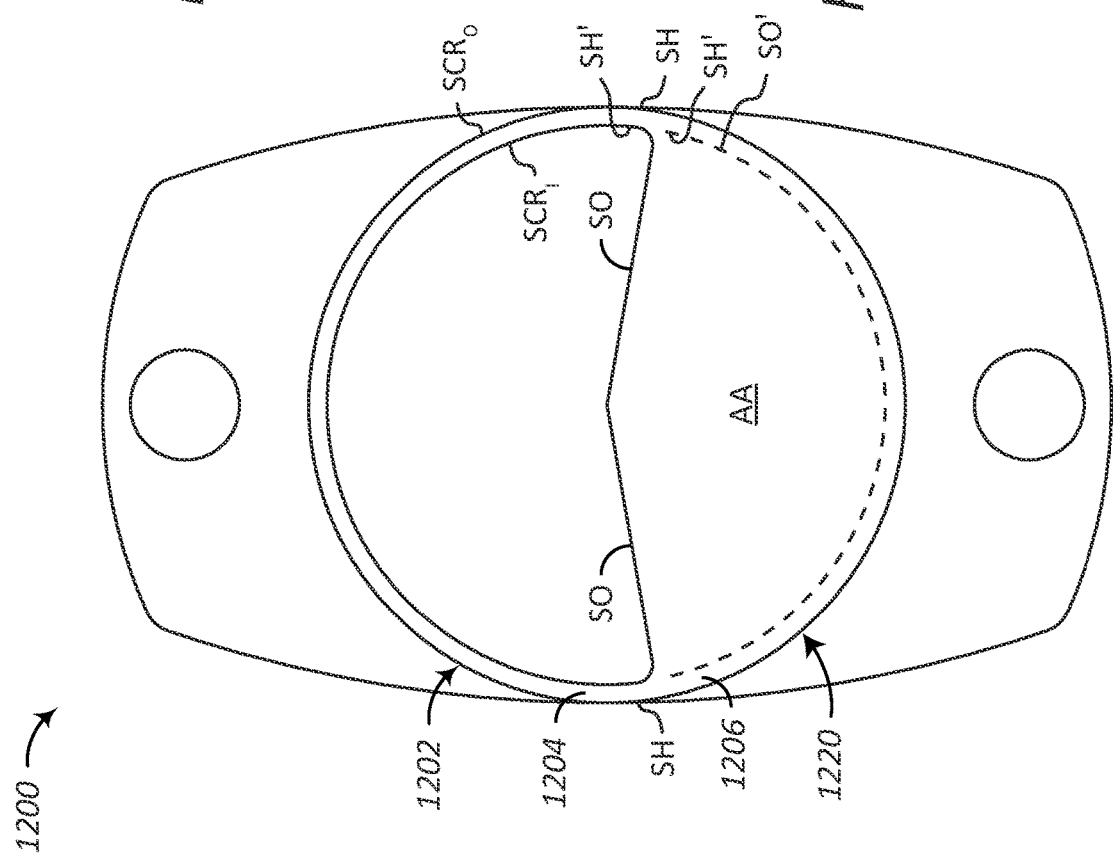

FIGS. 12A and 12B show an example embodiment of an optical device 1200 including a partial or incomplete optic 1220, such as or similar to the partial or incomplete optic 200 of FIGS. 2A and 2B, and a circumferential ring 1202 and plate haptics 1250 (the optical device 1200 and its partial or incomplete optic 1220, in various implementations, being of and embodying a lens/optic design that is configurable operatively to serve as or provide an add-on to an existing optical element or system). The circumferential ring 1202 includes an upper ring portion 1204 and a lower ring (/optic support) portion 1206 (e.g., shaped/configured as shown). The plate haptics 1250 include, at opposing exterior portions of the ring 1202, plate/arm elements 1252 that have or are provided with openings (or apertures) 1260 (e.g., shaped/configured as shown). The upper ring portion 1204 includes an inner surface (denoted "$SCR_I$") and an outer surface (denoted "$SCR_O$"). The partial or incomplete optic 1220 includes or is provided with edge or side portions, e.g., two symmetrical surfaces (each denoted "SO") and an adjoining curved surface (denoted "SO'", and shown in dashed lines). In at least one example embodiment, an (optical) active area (denoted "AA") (or an optically relevant portion) of the partial or incomplete optic 1220 has a (peripheral) boundary which, at least in part, includes or is defined by one or more edge or side portions/surfaces of the optic 1220 (such as for example the surfaces SO, SO'). The inner surface $SCR_I$ (of the upper ring portion 1204) together with the edge or side portion(s)/surface(s) SO (of the partial or incomplete optic 1220) define an opening 1230 (or an effectively optically irrelevant portion) of the partial or incomplete optic 1220.

FIGS. 13A and 13B show an example embodiment of an optical device 1300 including a partial or incomplete optic 1320, such as or similar to the partial or incomplete optic 200 of FIGS. 2A and 2B, and a circumferential ring 1302 and haptics 1350 configured to be iris-fixated (the optical device 1300 and its partial or incomplete optic 1320, in various implementations, being of and embodying a lens/optic design that is configurable operatively to serve as or provide an add-on to an existing optical element or system). The circumferential ring 1302 includes an upper ring portion 1304 and a lower ring (/optic support) portion 1306 (e.g., shaped/configured as shown). The haptics 1350 include, at opposing exterior portions of the ring 1302, plate/arm elements 1352 that have or are provided with openings (or apertures) 1360 (e.g., shaped/configured as shown). The haptics 1350 can include a slit 1370 (e.g., provided as shown) to serve as a claw to pinch onto the iris for fixation. The upper ring portion 1304 includes an inner surface (denoted "$SCR_I$") and an outer surface (denoted "$SCR_O$"). The partial or incomplete optic 1320 includes or is provided with edge or side portions, e.g., two symmetrical surfaces (each denoted "SO") and an adjoining curved surface (denoted "SO'", and shown in dashed lines). In at least one example embodiment, an (optical) active area (denoted "AA") (or an optically relevant portion) of the partial or incomplete optic 1320 has a (peripheral) boundary which, at least in part, includes or is defined by one or more edge or side portions/surfaces of the optic 1320 (such as for example the surfaces SO, SO'). The inner surface $SCR_I$ (of the upper ring portion 1304) together with the edge or side portion(s)/surface(s) SO (of the partial or incomplete optic 1320) define an opening 1330 (or an effectively optically irrelevant portion) of the partial or incomplete optic 1320.

Figure 14A:
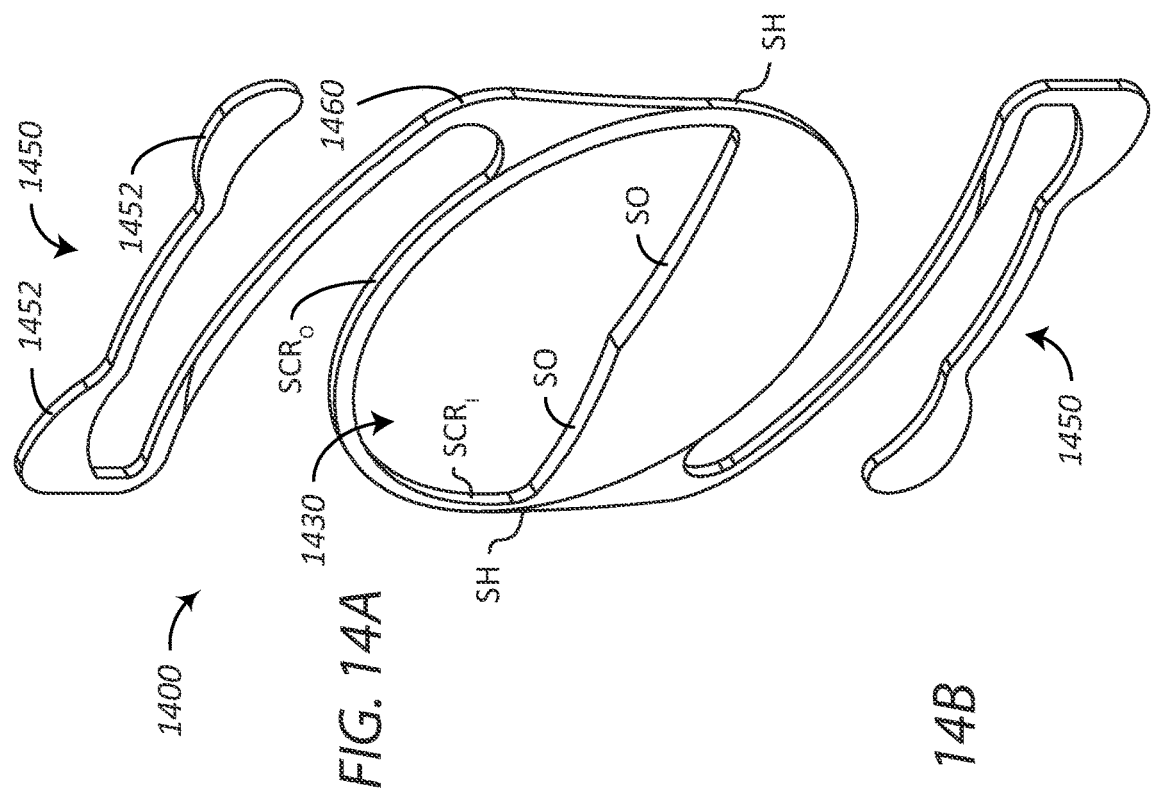
FIGS. 14A and 14B are perspective and plan views, respectively, of an example embodiment of an optical device including a partial or incomplete optic, such as or similar to that of FIGS. 2A and 2B, and a circumferential ring and haptics configured for anterior chamber positioning (the optical device and its partial or incomplete optic, in various implementations, being of and embodying a lens/optic design that is configurable operatively to serve as or provide an add-on to an existing optical element or system)
Figure 14B:
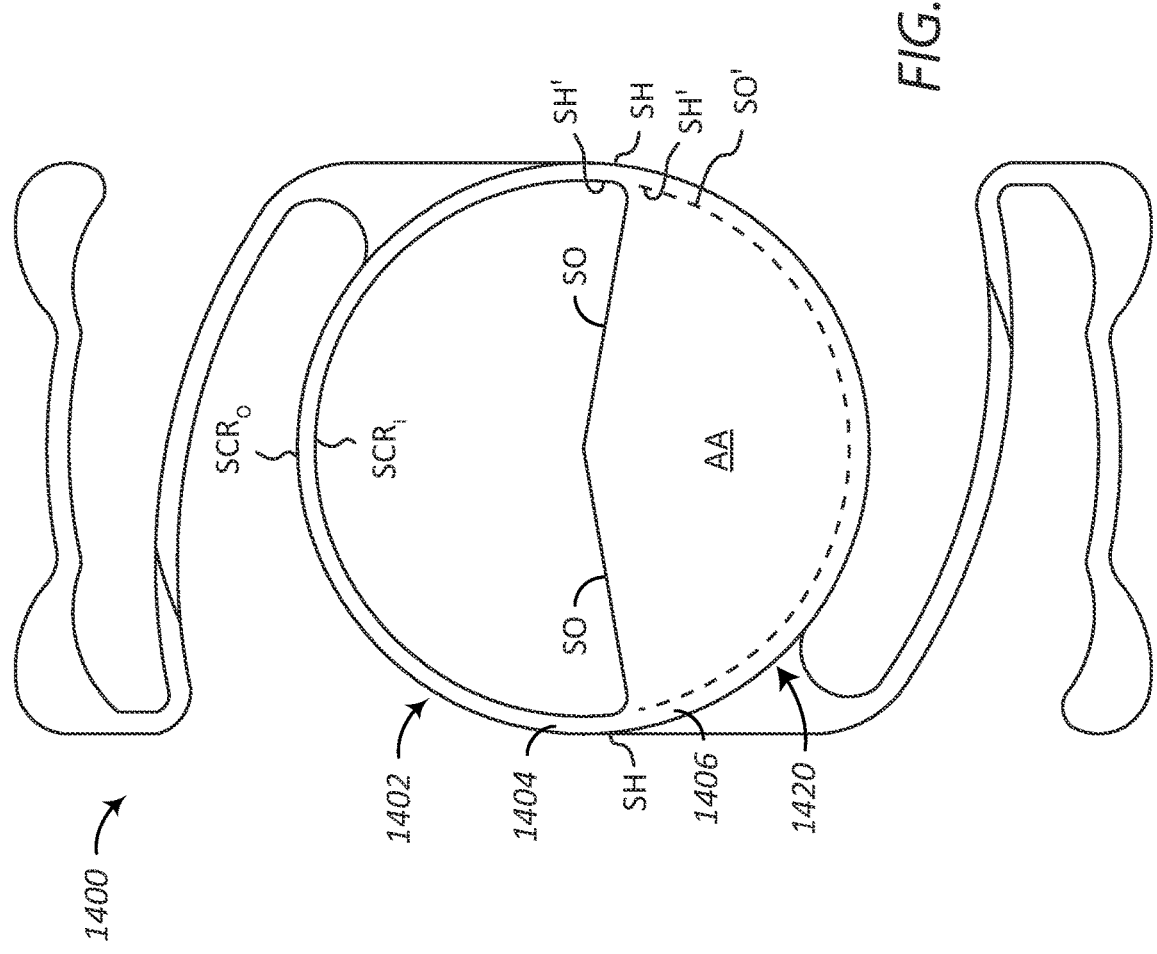

FIGS. 14A and 14B show an example embodiment of an optical device 1400 including a partial or incomplete optic 1420, such as or similar to the partial or incomplete optic 200 of FIGS. 2A and 2B, and a circumferential ring 1402 and haptics 1450 configured for anterior chamber positioning (the optical device 1400 and its partial or incomplete optic 1420, in various implementations, being of and embodying a lens/optic design that is configurable operatively to serve as or provide an add-on to an existing optical element or system). The circumferential ring 1402 includes an upper ring portion 1404 and a lower ring (/optic support) portion 1406 (e.g., shaped/configured as shown). The haptics 1450 include, at opposing exterior portions of the ring 1402, arms 1452 and base/interconnect elements 1460 (e.g., shaped/configured as shown). The upper ring portion 1404 includes an inner surface (denoted "$SCR_I$") and an outer surface (denoted "$SCR_O$"). The partial or incomplete optic 1420 includes or is provided with edge or side portions, e.g., two symmetrical surfaces (each denoted "SO") and an adjoining curved surface (denoted "SO'", and shown in dashed lines). In at least one example embodiment, an (optical) active area (denoted "AA") (or an optically relevant portion) of the partial or incomplete optic 1420 has a (peripheral) boundary which, at least in part, includes or is defined by one or more edge or side portions/surfaces of the optic 1420 (such as for example the surfaces SO, SO'). The inner surface $SCR_I$ (of the upper ring portion 1404) together with the edge or side portion(s)/surface(s) SO (of the partial or incomplete optic 1420) define an opening 1430 (or an effectively optically irrelevant portion) of the partial or incomplete optic 1420.

Thus, in example embodiments and implementations, an optical device includes: a partial or incomplete optic configured operatively as an add-on (e.g., supplemental lens/optic) for an (existing, as in already built/constructed/assembled, or already or previously installed) optical element or system, the partial or incomplete optic having an active area (or portion(s), e.g., one or more regions or sectors) configured in relation to the optical element or system such that the partial or incomplete optic controls or changes foci of light incident upon or provided to the active area, but does not control or change foci of light bypassing optically relevant portions of the partial or incomplete optic. In example embodiments and implementations, all portions of a partial or incomplete optic (i.e., the active area and periphery portion(s), if any, of the lens body) are considered to be "optically relevant" in that such portions affect light incident upon them (though in different ways). In embodiments/implementations in which periphery portion(s) of the lens body have no effect on the foci of light incident thereupon, or if the partial or incomplete optic does not include any periphery portion(s), in such cases, the "active area" would be the only "optically relevant" portion of the partial or incomplete optic.

With respect to optical devices including an opening that does not affect light passing therethrough (e.g., such as described with reference to FIGS. 10A-14B), such openings (or rather, the open space/area determined by and in relation to light effecting structure(s) that define the opening) are considered to be an "optically irrelevant" portions/areas of an optical device, or not optically relevant.

In example embodiments and implementations, the partial or incomplete optic is/includes a partial (optical) disc (e.g., an optic having substantially no more than a half circle body or optical zone).

In example embodiments and implementations, the optical device includes an opening (or an effectively optically irrelevant portion) adjacent to and/or not overlapping (any portion of) the active area. In example embodiments and implementations, such an opening encompasses a larger portion (e.g., viewed along optical axis) of the optical device than the active area—which is beneficial (at least in some implementations) in respect to halo management.

In example embodiments and implementations, the active area is (generally) fan-shaped (e.g., in a fan shape with a chord no more than twice the radius of the optical zone size)—also beneficial (at least in some implementations) in respect to halo management.

In example embodiments and implementations, the active area (e.g., a fan-shaped sector) is configured (e.g., in relation to the existing optical element or system) such that a line of sight (LOS) or a visual axis (VA) of or associated with the optical element or system is at or near a top portion of the active area (e.g., near top of fan sector).

In example embodiments and implementations, the partial or incomplete optic is configured (e.g., in relation to the existing optical element or system) such that the active area controls or changes foci of light incident upon or provided to the optical element or system at an optical region (or area) thereof (of the existing optical element or system). In example embodiments and implementations, the partial or incomplete optic is configured and in relation to the optical element or system such that the aforementioned optical region (or area) (of the existing optical element or system) is (generally) fan-shaped and/or at least partially (e.g., mostly) below (below, in elevational sense) a line of sight (LOS), and/or a visual axis (VA), of or associated with the optical element or system—beneficial (at least in some implementations) in respect to halo management.

As previously discussed, a partial or incomplete optic (e.g., such as or similar to that of FIGS. 2A and 2B) can be provided/configured operatively as an add-on lens/optic (e.g., in the form of an IOL and/or partial disc) that magnifies images via creating a near focal point, e.g., by adding a single power or a multifocal (sector) optic to an (existing) optical element or system. In example embodiments and implementations, a partial or incomplete optic is configured operatively as an add-on for an existing optical element or system to increase depth of focus. In example embodiments and implementations, a partial or incomplete optic is or includes an ophthalmic lens (e.g., configured to provide positive or negative optical power). The ophthalmic lens can include (or consist of) an optic having substantially one optical power, such as for example a monofocal clear lens. The ophthalmic lens can include (or consist of) a multifocal optic, such as for example a bifocal lens that controls or changes foci of light to enhance near and intermediate vision. In example embodiments and implementations, such a lens configured as an add-on to an (existing) optical element or system provides (or effectively provides) a trifocal optical device. In example embodiments and implementations, the active area is configured to provide an area- or sector-specific supplemental lens/optic that operates in conjunction with the optical element or system. In example embodiments and implementations, the active area includes (or consists of) one or more refractive optics or optical elements. In example embodiments and implementations, the active area includes (or consists of) one or more diffractive optics or optical elements. In example embodiments and implementations, the partial or incomplete optic is provided in the form of and/or includes at least a portion of an intraocular lens (IOL).

Example embodiments and implementations of the technologies and methodologies described herein involve a partial or incomplete optic having an active area that includes or is provided with one or more edge or side portions configured and/or treated to effect blocking (occlusion) or diffusion of light.

Figure 15A:
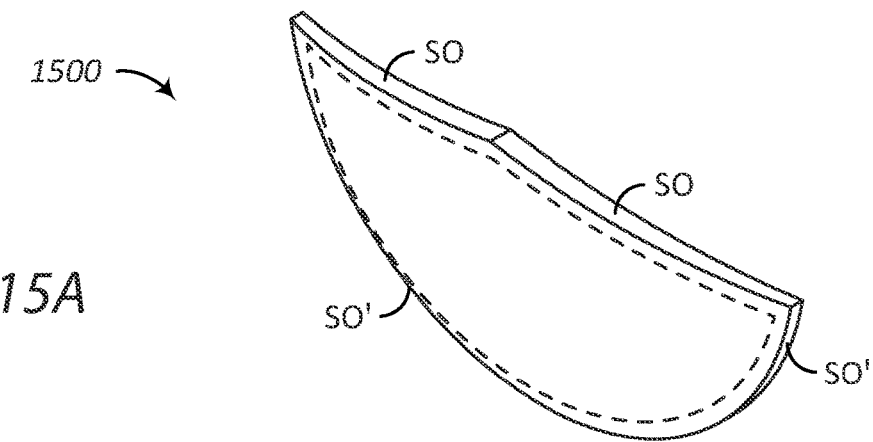
FIGS. 15A and 15B are perspective and plan views, respectively, of an example embodiment of a partial or incomplete optic, such as or similar to that of FIGS. 2A and 2B, the optic having a generally fan-shaped active area.
Figure 15B:
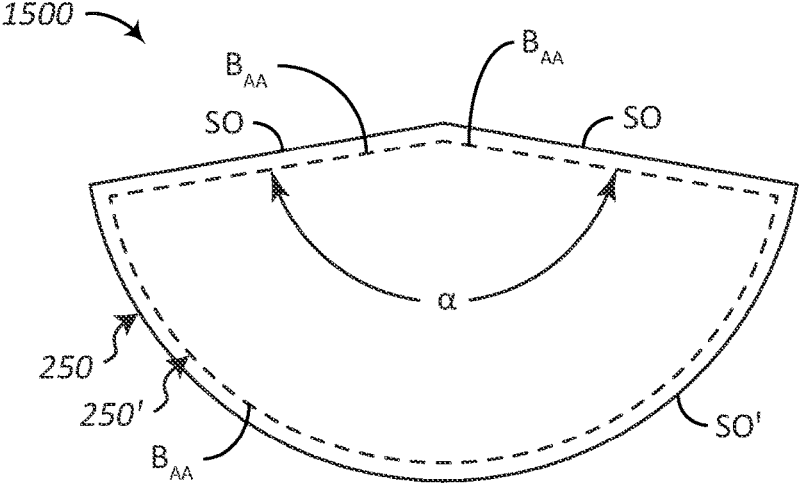

FIGS. 15A and 15B show an example embodiment of a partial or incomplete optic 1500 (e.g., such as or similar to the partial or incomplete optic 200) having a generally fan-shaped active area that includes or is provided with edge or side portions, e.g., including generally radially directed transitions/zones (denoted "SO" at their respective peripheral edge/side surfaces) and additionally, in some implementations, the (inferiorly facing) curved periphery portion (denoted SO' at its peripheral edge/surface), configured and/or treated (e.g., with a surface treatment or finish, e.g., a matte finish) to effect blocking (occlusion) or diffusion of light (i.e., stray light, specifically, transient bursts occurring as light sweeps horizontally across the aforementioned edge or side portions of the optical device, that otherwise could redirect into the fovea contributing to flare/glare). In example embodiments and implementations, an active area 250 of the partial or incomplete optic has a (peripheral) boundary which, at least in part, includes or is defined by one or more of the edge or side portions/surfaces SO, SO'.

In example embodiments and implementations, an active area 250' of the partial or incomplete optic has a (peripheral) boundary (shown in dashed lines, and denoted "$B_{AA}$"), which is at a distance from the edge or side surfaces SO, SO', the aforementioned distance by way of example being in a range of 0-0.5 mm. In other words, in some implementations, the active area peripheral boundary $B_{AA}$ is or includes (or is co-extensive with) the edge or side surfaces SO, SO', while in other implementations, the active area peripheral boundary $B_{AA}$ is a distance from (e.g., not intersecting or directly adjacent to) the edge or side surfaces SO, SO'. Thus, in example embodiments and implementations (such as those described herein in which the active area is generally fan-shaped, or a modification of such a shape), the active area peripheral boundary $B_{AA}$ includes generally radially directed segments that define (in relation to each other) an angle $\alpha$ which can be referred to as the angular width of the active area. By way of example, for a (generally) fan-shaped active area, the angular width $\alpha$ can be 45° to 180°. As previously discussed, in some implementations, a pair of generally radially directed (e.g., symmetrical) segments of the active area peripheral boundary $B_{AA}$ overlay or are substantially co-extensive with the edge or side surfaces SO, in which case, the generally radially directed peripheral edge/side surfaces SO (at either side of the active area) also define or approximately define (in relation to each other) an angle $\alpha$ which can be referred to as the angular width of the active area.

Thus, in example embodiments and implementations involving a partial or incomplete optic that includes an active area (e.g., such as described herein), the active area includes or is provided with edge or side portions (e.g., generally radially directed transitions/zones) configured and/or treated to effect blocking (occlusion) or diffusion of light (i.e., stray light, specifically, transient bursts occurring as light sweeps horizontally across the aforementioned edge or side portions, that otherwise could redirect into the fovea contributing to flare/glare).

In example embodiments and implementations, the edge or side portions include or are provided as a light absorbing surface layer (e.g., that absorbs at least a portion of the light wavelength in the visible spectrum (400 nm-700 nm) at the edge or side portions). In example embodiments and implementations, the edge or side portions include or are provided as a surface (roughness/modification) treatment applied or provided (at the edge or side portions) such that gloss expressed at the edge or side portions is less than a (maximum/predetermined/selected/specified) gloss unit (GU) value (e.g., <30 GU) or values (or range or gradient of values, or multiple different values, e.g., at different surfaces respectively of the edge or side portions) specified in respect to (or otherwise associated with) the edge or side portions. In example embodiments and implementations, the edge or side portions include or are provided as a surface finish applied or provided (at the edge or side portions) such that surface roughness at the edge or side portions has (is characterized by) peak-valley height values (within a range) of 7-15 microns.

Figure 20:
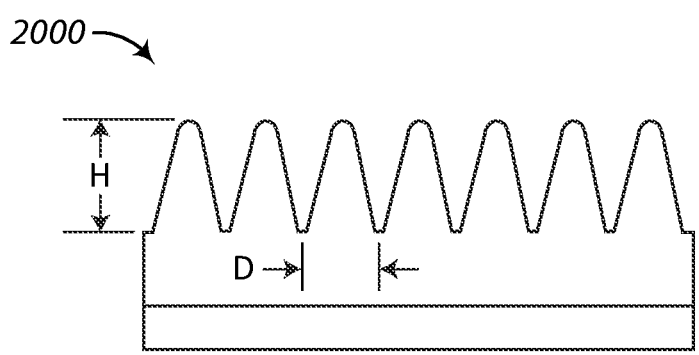
FIG. 20 is an illustration of an edge or side portion (e.g., of an active area of a partial or incomplete optic, or of a haptic or support structure) including or provided with nano-structures that block or diffuse light incident thereupon.

The edge or side portions that block (occlude) or diffuse light can include or be provided in the form of nano-structures, e.g., nano-tips (cones). Nano-structures, for purposes of this application, are or can be defined as structures having at least one feature dimension (e.g., a tip base diameter size) that is in the 0.1 to 1000 nm range. FIG. 20 is an illustration of an edge or side portion (e.g., of an active area of a partial or incomplete optic) including or provided with nano-structures 2000 that are cone-shaped or approximately cone-shaped (e.g., nano-tips (cones)), the nano-structures (or nano-tips or cones thereof) being, for example, 100-300 nm in base diameter (D) and 1,000-16,000 nm (i.e., 1-16 microns) in height (H). In example embodiments and implementations, the edge or side portions include or are provided as nano-structures that have nano-tips or cones. In example embodiments and implementations, the edge or side portions include or are provided as nano-structures that are cone-shaped or approximately cone-shaped and/or nano-structures including cone-shaped or generally cone-shaped portions. Such nano-structures can include, for example: nano-tips (e.g., nano-structures that are cone-shaped or approximately cone-shaped and/or nano-structures including cone-shaped or generally cone-shaped portions), nano-arrays (of cones, for example, or of nano-structures having/including other shapes), aperiodic or other arrays of nano-structures (e.g., nano-tips), antireflection structures (e.g., antireflection nano-structures that have nano-tips, cone-arrays), biomimetic structures (e.g., biomimetic nano-tips or other nano-structures, biomimetic antireflection structures), or a combination or combinations thereof. See also Liu F, Dong B and Liu X 2012 Optical devices in communication and computation (Bio-inspired photonic structures: prototypes, fabrications and devices) ed P Xi (Rijeka, Croatia: Intech) pp. 107-126, which is hereby incorporated by reference.

Figure 16:
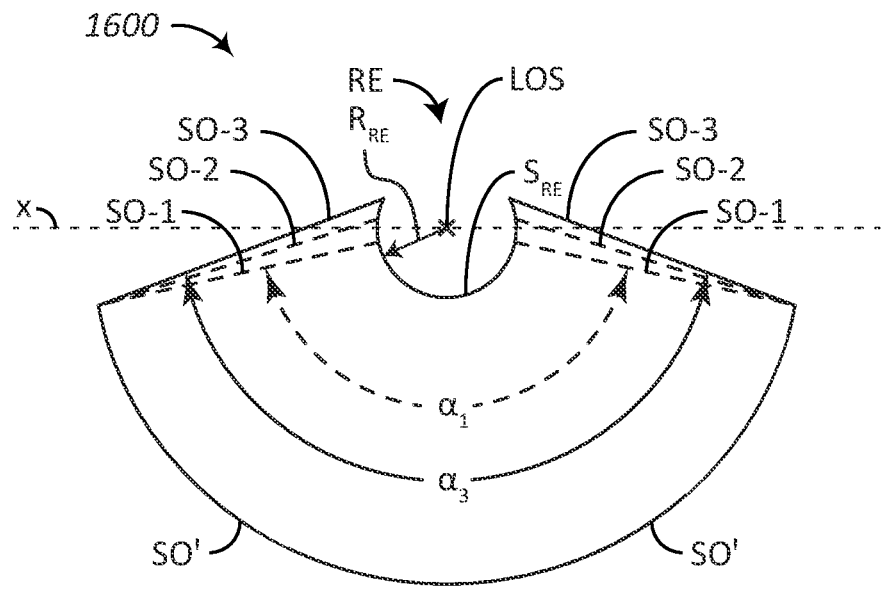
FIG. 16 is a plan view of another example embodiment of a partial or incomplete optic also having a generally fan-shaped active area though differing (from the optic shown in FIGS. 15A and 15B) in that the active area of optic includes or is provided with an additional edge portion or surface, namely, a concave edge surface (or recess) (denoted "RE").

FIG. 16 is a plan view of an example embodiment of a partial or incomplete optic 1600 also having a generally fan-shaped active area though differing (from the optic shown in FIGS. 15A and 15B) in that the active area of optic 1600 includes or is provided with an additional edge portion or surface, namely, a recess denoted "RE" having and defined at least in part by concave edge portion(s)/surface(s) denoted "$S_{RE}$", which provide(s) the partial or incomplete optic 1600 with an opening through which light can pass (e.g., to another optical element or system) without being effected by the (active area of the) optic 1600. The concave edge portion/surface $S_{RE}$ (of the recess RE), shown in profile and defined by radius $R_{RE}$ in the example embodiment depicted in FIG. 16, has the appearance of a portion of a circle or other curve, or of an inside surface of a partial cylinder, tube, or other curved structure. The concave edge portion/surface $S_{RE}$ can be, but is not necessarily, concentric with respect to the (inferiorly facing) periphery edge or side portion/surface SO'.

Figure 17:
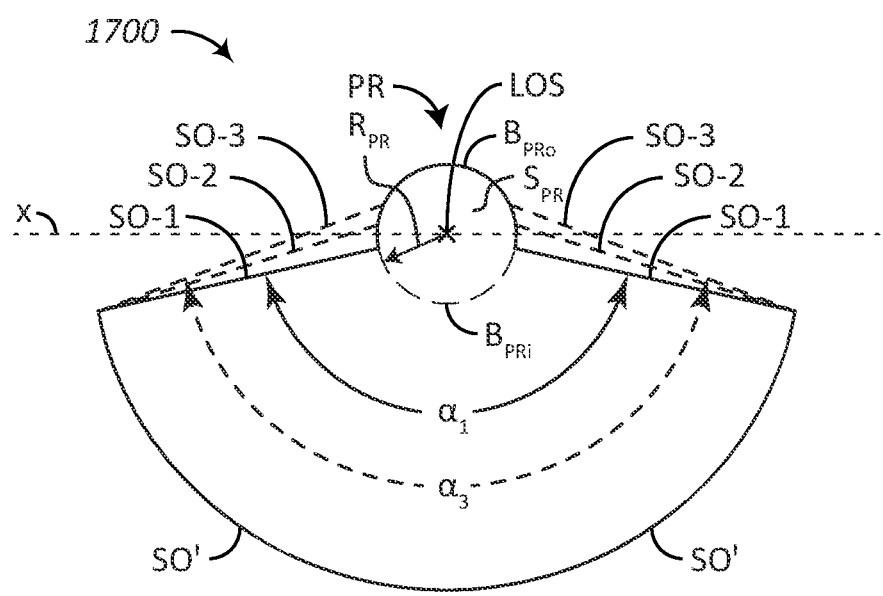
FIG. 17 is a plan view of another example embodiment of a partial or incomplete optic also having a generally fan-shaped active area though differing (from the optic shown in FIGS. 15A and 15B) in that the active area of optic includes or is provided with an additional edge portion or surface, namely, a convex edge surface (or protrusion) (denoted "PR").

FIG. 17 is a plan view of an example embodiment of a partial or incomplete optic 1700 also having a generally fan-shaped active area though differing (from the optic shown in FIGS. 15A and 15B) in that the active area of optic 1700 includes or is provided with an additional lens portion or sector, namely (in relation to the generally fan-shaped active area of the optic), a protrusion denoted "PR" having and defined at least in part by a lens surface denoted "$S_{PR}$", protrusion outer edge portion(s)/surface(s) denoted "$B_{PRo}$", and protrusion inner edge portion(s)/surface(s) denoted "$B_{PRi}$" (shown in dashed lines). In the example embodiment depicted in FIG. 17, the outer and inner edge portion(s)/surface(s) $B_{PRo}$, $B_{PRi}$, (of the protrusion PR) are shown in profile and defined by radius $R_{PR}$. The additional circular lens portion or sector $S_{PR}$ can be configured for example to provide added/increased magnification power. The protrusion inner edge portion(s)/surface(s) $B_{PRi}$ (at which the protrusion PR and the generally fan-shaped active area of the optic 1700 interface/transition) can be, but is not necessarily, concentric with respect to the (inferiorly facing) periphery edge or side portion/surface SO'.

The centration or other positioning strategy/approach utilized for an optical device including a partial or incomplete optic can be selected or determined depending upon considerations particular to the existing optical element or system (in/including an eye) and the nature of the optical device that is to be provided as a supplemental lens/optic. An optical device including a partial or incomplete optic can be centered and/or otherwise positioned/oriented in relation to one or more axes of or associated with the optical element or system (e.g., an optical axis of an existing optical element with which the partial or incomplete optic is to be configured operatively as an add-on). In the case of an optical system that includes an eye, an optical device including a partial or incomplete optic can be centered and/or otherwise positioned/oriented (e.g., determining optimal (de)centration and tilt for a partial or incomplete optic in the form of an IOL) in relation to, for example: a line of sight (LOS), a visual axis (VA) or approximation thereof, a pupillary axis, a supranasal axis, another axis of or associated with the eye (e.g., centered on the achromatic visual axis of an eye, somewhere between the first Purkinje image and the pupillary center), or a combination of these axes. Further, the strategy/approach can be selected or determined for the clockwise or counterclockwise rotation about the LOS or VA depending upon or in consideration of patient preference of halos orientations. For example, some patients may prefer to see the halos are in the superior instead of inferior visual field. See also Bonaque-Gonzales et al, 2015, Influence on visual quality of intraoperative operative operation of Asymmetric Intraocular Lenses J. Refract Surg. 2015, 31, pp. 651-656, which is hereby incorporated by reference.

Line of sight (LOS), for purposes of this application, is or can be an axis defined in relation to an aperture (or other component) of an optical element or system, such as the pupil of an eye. For example, LOS can be an axis defined by the geometric center of a pupil (e.g., intersecting the geometric center of the undilated pupil). Visual axis (VA), for purposes of this application, is or can be an axis defined in relation to a fixation point and light sensor(s) of an optical element or system, such as the fovea of an eye. In the case of an optical system that includes an eye, VA can be, for example, a path or line extending from a fixation point (through the nodal points) to the fovea. Corneal vertex can be utilized, in some implementations, as an approximation of the visual axis (VA). A pupillary axis is a pathway that extends through the center of the entrance pupil and is perpendicular to the corneal point that it transects. A supranasal axis is an axis that is (de)centered somewhere between the pupillary axis and the visual axis. See also Roach, L "Centration of IOLs: Challenges, Variables, and Advice for Optimal Outcomes" *EyeNet* April 2013 pp. 39-41, which is hereby incorporated by reference.

The previous discussion (with reference to FIGS. 15A and 15B) regarding the active area peripheral boundary $B_{AA}$ of partial or incomplete optics is also applicable, in example embodiments/implementations, to partial or incomplete optics including or involving an active area boundary/edge recess (such as, for example, the partial or incomplete optic 1600 in FIG. 16) and particularly in respect to the edge or side portions/surfaces SO (of the generally fan-shaped active area). Optics including or involving an active area boundary/edge recess can be provided in various designs, for example, as depicted in FIG. 16, in which the concave edge portion/surface $S_{RE}$ and the edge or side portions/surfaces SO differ in their positions and orientations (in relation to for example LOS and horizontal axis "x", respectively), and in some instances, the length/radial span of the edge or side portions/surfaces SO of the optic 1600 differ (e.g., are shorter, or possibly longer), depending, for example, upon the dimensions of the recess RE and of the optic 1600 overall and particulars of how the optic is to be configured with and in relation to another optical element or system.

Further as to examples of how the optic 1600 can be configured with and in relation to another (e.g., existing) optical element or system, see also the previous discussions (e.g., with reference to FIGS. 4 and 7 and otherwise) regarding the location of a partial or incomplete optic in relation to a line of sight (LOS), and/or visual axis (VA), associated with the optical element or system.

For example, in at least one implementation in relation to FIG. 16, $R_{RE}$ is approximately in the range of 0.5 mm to 1.0 mm, for a partial or incomplete optic located in the eye, at a distance of 1.5 mm anteriorly from the existing lens and positioned at about 0.2 mm nasal and 0.1 mm inferior in relation to a visual axis of the eye.

The previous discussion (with reference to FIGS. 15A and 15B) regarding the active area peripheral boundary $B_{AA}$ of partial or incomplete optics is also applicable, in example embodiments/implementations, to partial or incomplete optics including or involving active area boundary/edge protrusion (such as, for example, the partial or incomplete optic 1700 in FIG. 17) and particularly in respect to the edge or side portions/surfaces SO (of the generally fan-shaped active area). Optics including or involving active area boundary/edge protrusion can be provided in various designs, for example, as depicted in FIG. 17, in which the convex edge portion/surface $B_{PRo}$ and the edge or side portions/surfaces SO differ in their positions and orientations (in relation to, for example, LOS and horizontal axis "x", respectively), and in some instances, the length/radial span of the edge or side portions/surfaces SO of the optic 1700 differ (e.g., are shorter, or possibly longer), depending, for example, upon the dimensions of the protrusion PR and of the optic 1700 overall and particulars of how the optic is to be configured with and in relation to another optical element or system.

Further as to examples of how the optic 1700 can be configured with and in relation to another (e.g., existing) optical element or system, see also the previous discussions (e.g., with reference to FIGS. 4 and 7 and otherwise) regarding the location of a partial or incomplete optic in relation to a line of sight (LOS), and/or visual axis (VA), associated with the optical element or system.

For example, in at least one implementation in relation to FIG. 17 embodiment, $R_{PR}$ is approximately in the range of 0.5 mm to 1.0 mm, for a partial or incomplete optic located in the eye, at a distance of 1.8 mm anteriorly from the existing lens and positioned/centered on a visual axis of the eye.

Figure 18:
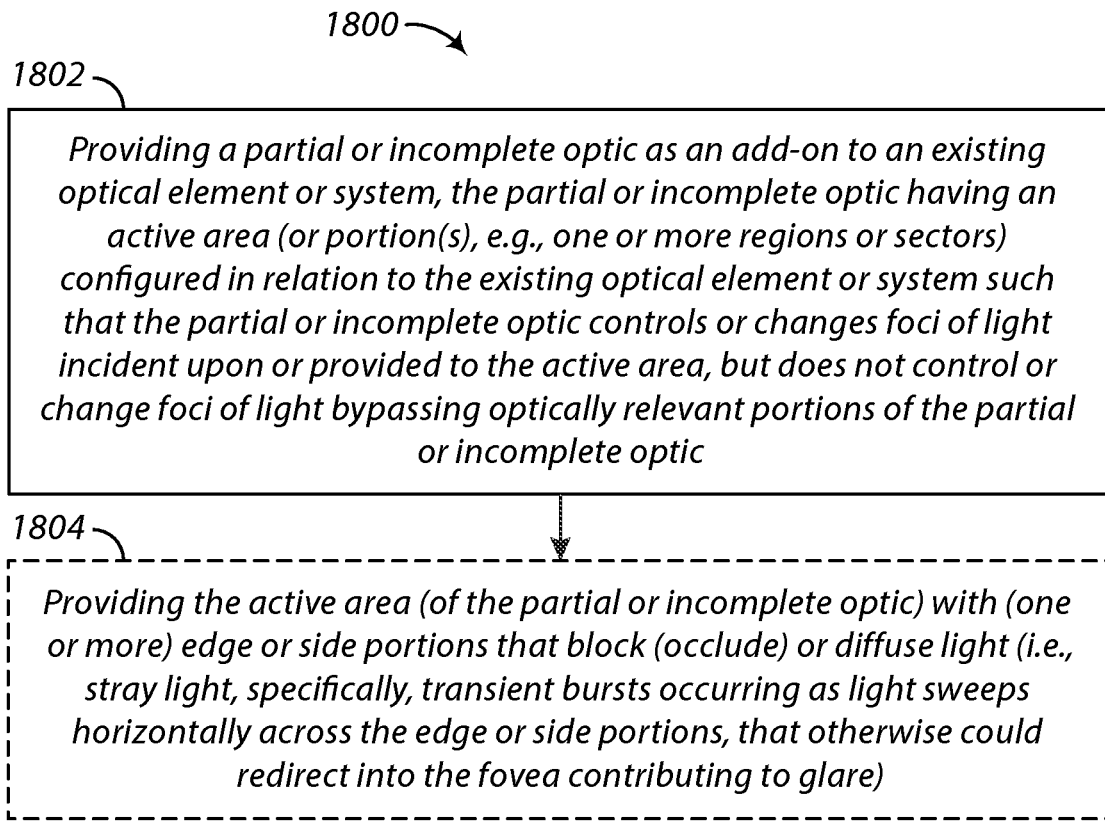
FIG. 18 is a flow diagram of an example method for enhancing vision.

Referring to FIG. 18, an example method 1800 for enhancing vision includes, at 1802, providing a partial or incomplete optic as an add-on to an existing optical element or system, the partial or incomplete optic having an active area (or portion(s), e.g., one or more regions or sectors) configured in relation to the existing optical element or system such that the partial or incomplete optic controls or changes foci of light incident upon or provided to the active area, but does not control or change foci of light bypassing optically relevant portions of the partial or incomplete optic.

The step of providing (e.g., implanting) a partial or incomplete optic includes, for example, positioning the partial or incomplete optic in relation to the existing optical element or system such that the active area controls or changes foci of light incident upon or provided to the existing optical element or system at an optical region (or area) thereof (of the existing optical element or system). In example embodiments and implementations, the optical region (or area) (of the existing optical element or system) is (generally) fan-shaped and/or at least partially (e.g., mostly) below (below, in elevational sense) a line of sight (LOS) or a visual axis (VA) of or associated with the existing optical element or system.

In example embodiments and implementations, the existing optical element or system includes a lens (or other optic) implanted in an eye (e.g., a human eye) (or other seeing mechanism or device); and the step of providing a partial or incomplete optic is performed subsequent to the lens (or other optic) being implanted.

In example embodiments and implementations, the existing optical element or system includes a lens (or other optic) implanted in an eye (e.g., a human eye); and the step of providing a partial or incomplete optic includes positioning (e.g., implanting) the partial or incomplete optic in the eye at a location, the location being: in front of an iris/within an anterior chamber (of the eye), at or near an iris (of the eye), behind an iris/in sulcus (of the eye), or inside a capsular bag (of the eye).

In example embodiments and implementations, the existing optical element or system includes a lens (or other optic) implanted in an eye (e.g., a human eye); and the step of providing a partial or incomplete optic includes utilizing one or more portions of the eye to secure (e.g., utilizing one or more clip, claw, anchor, haptic or support structure) the partial or incomplete optic within the eye, the portion(s) of the eye including one or more of: an iris, an anterior chamber, a sulcus (e.g., IOL placement/fixation in the sulcus, ciliary sulcus implantation), and a capsular bag (e.g., IOL placement in the capsular bag).

In example embodiments and implementations, the method 1800 (and referring again to FIG. 18) further includes, at 1804, providing the active area (of the partial or incomplete optic) with (one or more) edge or side portions that block (occlude) or diffuse light (i.e., stray light, specifically, transient bursts occurring as light sweeps horizontally across the edge or side portions, that otherwise could redirect into the fovea contributing to flare/glare).

Figure 19:
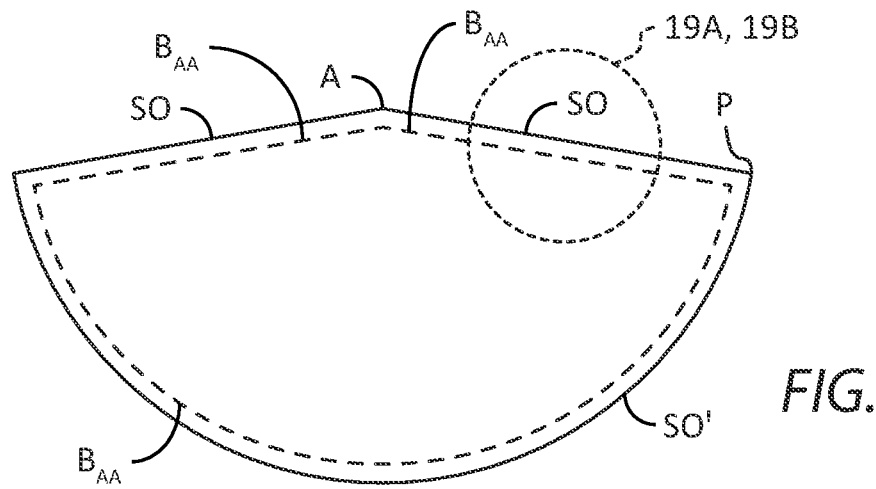
FIG. 19 is a plan view of an example embodiment of a partial or incomplete optic, such as or similar to that of FIGS. 2A and 2B, the optic having a generally fan-shaped active area and edge or side portions.
Figure 19A:
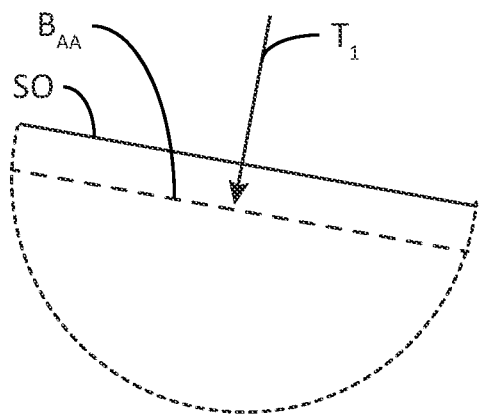
FIG. 19A is an enlarged partial view of the optic of FIG. 19, including a pictorial representation of a process of applying a light effecting treatment, finish or other modification (from outside inward, as represented by the arrow denoted "$T_1$") to provide the active area with edge or side portions that block or diffuse light.
Figure 19B:
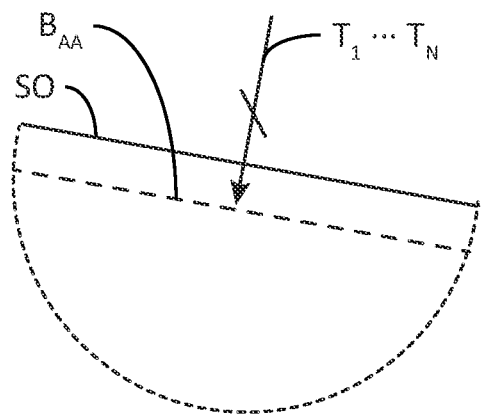
FIG. 19B is an enlarged partial view of the optic of FIG. 19, including a pictorial representation of a process or processes of utilizing multiple light effecting treatments, finishes and/or other modifications (from outside inward, as represented by the arrow, in plural form, denoted "$T_1 \bullet \bullet \bullet T_N$") to provide the active area with edge or side portions that block or diffuse light.
Figure 19C:
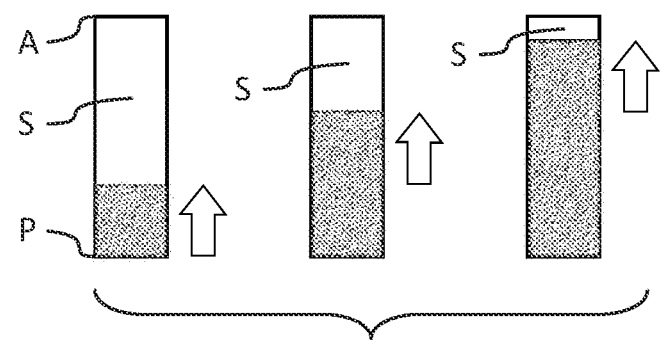
FIG. 19C shows, in a series of illustrations, an edge or side portion (e.g., of an active area of a partial or incomplete optic, or of a haptic or support structure) to which a light effecting treatment, finish or other modification is directionally applied (along surface S, as represented by the arrow repositioning from the periphery of the optic inward)

In example embodiments and implementations, the step of providing edge or side portions that block (occlude) or diffuse light includes applying a surface treatment or finish (e.g., a matte finish) at the edge or side portions from outside-in without affecting optical areas. Referring to FIG. 19, the edge or side portions/surfaces SO, SO' (of the partial or incomplete optic 1500) include/define an apex (denoted "A") between the two portions/surfaces SO, and periphery junctures (denoted "P") where the portions/surfaces SO each adjoin the edge or side portion/surface SO', respectively. The partial or incomplete optic 1500 includes an active area (denoted "AA"). FIG. 19A is an enlarged partial view of the optic of FIG. 19, including a pictorial representation of a process of applying a light effecting treatment, finish or other modification (from outside inward, as represented by the arrow denoted "$T_1$") to provide the active area with edge or side portions that block or diffuse light. FIG. 19B is an enlarged partial view of the optic of FIG. 19, including a pictorial representation of a process or processes of utilizing multiple light effecting treatments, finishes and/or other modifications (from outside inward, as represented by the arrow, in plural form, denoted "$T_1 \cdots T_N$") to provide the active area with edge or side portions that block or diffuse light. In example embodiments and implementations, such processes are applied from outside inward, but not impinging upon or extending further (in their light occluding or influencing effects) than the active area boundary $B_{AA}$. Additionally, in example embodiments and implementations, the step of providing edge or side portions that block (occlude) or diffuse light includes or involves a light effecting treatment, finish or other modification that is directionally applied (e.g., along, or otherwise in relation to, edge or side portion(s)/surface(s)). FIG. 19C shows, in a series of illustrations, an edge or side portion (e.g., of an active area of a partial or incomplete optic, or of a haptic or support structure) to which a light effecting treatment, finish or other modification is directionally applied along surface S thereof, as represented by the arrow (e.g., repositioning from the periphery P of the optic inward toward the apex A, or vice versa).

In example embodiments and implementations, the step of providing edge or side portions that block (occlude) or diffuse light includes applying a light absorbing surface layer (e.g., that absorbs at least a portion of the light wavelength in the visible spectrum (400 nm-700 nm)) at the edge or side portions. In example embodiments and implementations, the step of providing edge or side portions that block (occlude) or diffuse light includes applying a surface (roughness/modification) treatment at the edge or side portions such that gloss expressed at the edge or side portions is less than a (maximum/predetermined/selected/specified) gloss unit (GU) value (e.g., <30 GU) or values (or range or gradient of values, or multiple different values, e.g., at different surfaces respectively of the edge or side portions) specified in respect to (or otherwise associated with) the edge or side portions. In example embodiments and implementations, the step of providing edge or side portions that block (occlude) or diffuse light includes applying a surface finish at the edge or side portions (e.g., milling the edge and/or side portions) such that surface roughness at the edge or side portions has (is characterized by) peak-valley height values (within a range) of 7-15 microns.

In example embodiments and implementations, the step of providing edge or side portions that block (occlude) or diffuse light includes utilizing one or more of: a lithography technique (e.g., colloidal lithography), an etching technique (e.g., a plasma etching technique such as Electron cyclotron resonance (ECR) plasma etching, reaction ion etching (RIE)), or a (self-masked) dry etching technique), and an UV/Ozone surface treatment (See U.S. Pat. No. 8,088,314 B2, which is hereby incorporated by reference), to apply and/or modify one or more surface structures at the edge or side portions. For example, an etching technique (e.g., a plasma etching technique) can be utilized to provide (e.g., apply and/or modify) one or more surface structures at the edge or side portions. In example embodiments and implementations, surface modifications are applied or made at edge and/or side portions of a partial or incomplete optic made of (or that includes) a hydrophobic acrylic polymer.

In example embodiments and implementations, the step of providing edge or side portions that block (occlude) or diffuse light includes providing nano-structures, e.g., nano-tips (cones), at the edge or side portions. Such nano-structures can include, for example: nano-tips (e.g., nano-structures that are cone-shaped or approximately cone-shaped and/or nano-structures including cone-shaped or generally cone-shaped portions), nano-arrays (of cones, for example, or of nano-structures having/including other shapes), aperiodic or other arrays of nano-structures (e.g., nano-tips), antireflection structures (e.g., antireflection nano-structures that have nano-tips, cone-arrays), biomimetic structures (e.g., biomimetic nano-tips or other nano-structures, biomimetic antireflection structures), or a combination or combinations thereof. See also Liu F, Dong B and Liu X 2012 Optical devices in communication and computation (Bio-inspired photonic structures: prototypes, fabrications and devices) ed P Xi (Rijeka, Croatia: Intech) pp. 107-126, which is hereby incorporated by reference.

As previously discussed with reference to FIG. 20, the nano-structures can be cone-shaped or approximately cone-shaped (e.g., nano-tips (cones)), the nano-structures (or nano-tips or cones thereof) being, for example, 100-300 nm in base diameter (D) and 1,000-16,000 nm (i.e., 1-16 microns) in height (H). In example embodiments and implementations, the step 1804 (FIG. 18) of providing edge or side portions that block (occlude) or diffuse light includes providing (at the edge or side portions) nano-structures that are cone-shaped or approximately cone-shaped (e.g., nano-tips (cones)), the nano-structures being 100-300 nm in base diameter and 1,000-16,000 nm (i.e., 1-16 microns) in height (and/or nano-structures including cone-shaped or generally cone-shaped portions).

In example embodiments and implementations, the techniques and processes discussed herein can additionally, or alternatively, be utilized to provide a light effecting treatment, finish or other modification for other portions/surfaces of an optical device. For example, and referring again to FIGS. 10A-14B, inside portions/surfaces (denoted SH') of a haptic or support structure (e.g., above or below the periphery of SO adjacent the haptic, or both) can also receive one or more light effecting treatments, finishes and/or other modifications that block or diffuse light incident thereupon.

The techniques and processes for providing light effecting treatments, finishes and/or other modifications discussed herein can also be utilized (e.g., as applicable depending upon the optically relevant or potentially relevant portions/ surfaces of a partial or incomplete optic and particulars regarding how the optic is to be configured with and in relation to an optical element or system) for other portions/surfaces of lens/optics designs, for example, in relation to the edge or side portions/surfaces of the recess RE (FIG. 16) and of the protrusion PR (FIG. 17).

In other example embodiments and implementations, the optical device further includes one or more clip, claw, anchor, haptic or support structure, one or more portions of which is/are configured and/or treated (e.g., with a surface treatment or finish, e.g., a matte finish) to effect blocking (occlusion) or diffusion of light (i.e., stray light, specifically, transient bursts occurring as light sweeps horizontally across the aforementioned edge or side portions of the optical device, that otherwise could redirect into the fovea contributing to flare/glare).

By way of example, and referring again to FIGS. 10A-14B, one or more portions/surfaces of the haptic or support structure(s) in these and other example optical devices can be configured and/or treated (e.g., in addition to, or as an alternative to, providing the light effecting treatments, finishes and/or other modifications at the edge or side portions/surfaces SO and/or at the (inferiorly facing) periphery edge or side portion/surface SO' of the partial or incomplete optic) to effect blocking (occlusion) or diffusion of light. Such portions/surfaces of the haptics are denoted "SH" (for illustrative purposes only at opposite left and right periphery portions/surfaces of the haptics as shown in FIGS. 10A-14B) and include, for example, portions/surfaces tending, without light effecting treatment/modification, to contribute to glare. In some implementations, such portions/surfaces of the haptics include vertical portions/surfaces in relation to, and/or peripheral portions/surfaces intersecting (or other portions/surfaces actually or potentially optically relevant in relation to), a line of sight (LOS) and/or a visual axis (VA) (e.g., of or associated with an existing optical element or system with which the partial or incomplete optic is configured operatively). In this context, the LOS for example can be considered as being within a horizontal plane in relation to which the orientation of the aforementioned vertical portions/surfaces is orthogonal (or perpendicular). A horizontal line (such as the axis denoted "x" in FIG. 5, 16 or 17) perpendicular to and intersecting the LOS can be utilized to (at least conceptually) provide a boundary separating upper and lower (or superior and inferior) portions of the partial or incomplete optic. Such a horizontal line can also be, for example, in a plane at (i.e., passing through) and representative of the orientation of the partial or incomplete optic. Also within this context, a horizontal reference (such as a line or a plane) can be defined in relation to an optical element or system with which the partial or incomplete optic is configured operatively (e.g. as being fixed in relation to the optical element or system) or in relation to the partial or incomplete optic (e.g. as being fixed in relation to the partial or incomplete optic).

In some circumstances, it may be useful to define directions/orientations in relation to an operating environment of and in respect to imaging elements (image acquisition) functionalities of an optical element or system and/or the partial or incomplete optic. For example, a horizontal reference (such as a line or a plane) alternatively can be defined in relation to an environment containing objects that can be visually perceived (and in this respect, oncoming headlights are emblematic) by an optical element or system with which the partial or incomplete optic is configured operatively. In such a system of reference, that which (in direction or orientation) is considered "vertical", for example, changes (in relation to portion(s)/structure(s) of the partial or incomplete optic) as the optical element or system (with which the partial or incomplete optic is configured) reorients (redirecting LOS/VA) in relation to the operating environment.

Figure 21A:
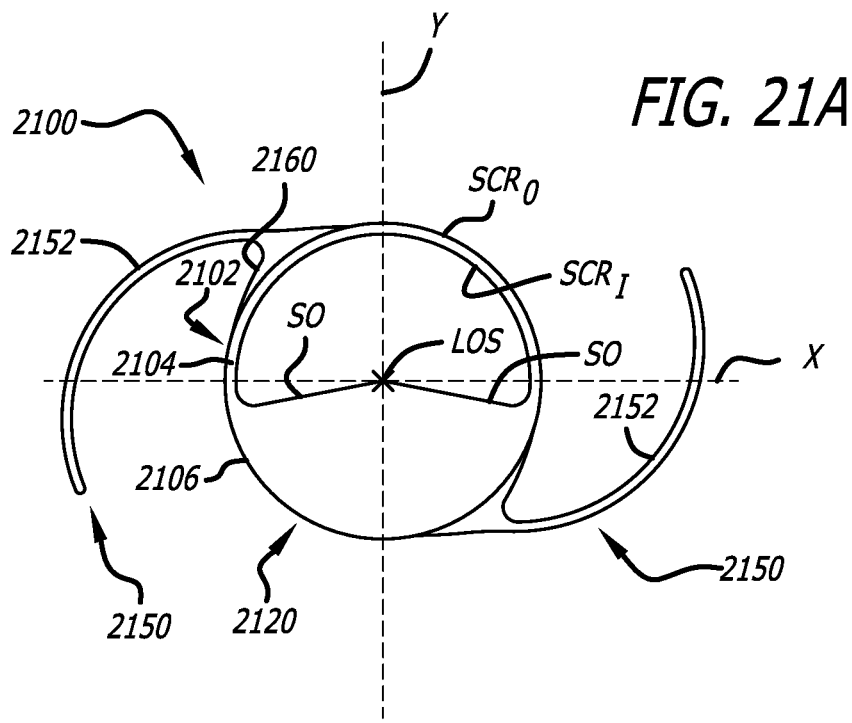
FIG. 21A is a plan view of an example embodiment of an optical device including a partial or incomplete optic, such as or similar to that of FIGS. 2A and 2B, and a circumferential ring and loop haptics, such as or similar to those of the optical device of FIGS. 11A and 11B (the optical device and its partial or incomplete optic, in various implementations, being of and embodying a lens/optic design that is configurable operatively to serve as or provide an add-on to an existing optical element or system), the optical device being configured and the partial or incomplete optic and the circumferential ring being made of a material or materials sufficiently soft (e.g., a soft acrylic material) to permit the optical device to be folded for installing (e.g., implanting) the optical device in an eye (e.g., a human eye) or other seeing mechanism or device that operatively interfaces/provides an operative interface with the haptics (when the optical device is installed)
Figure 21B:
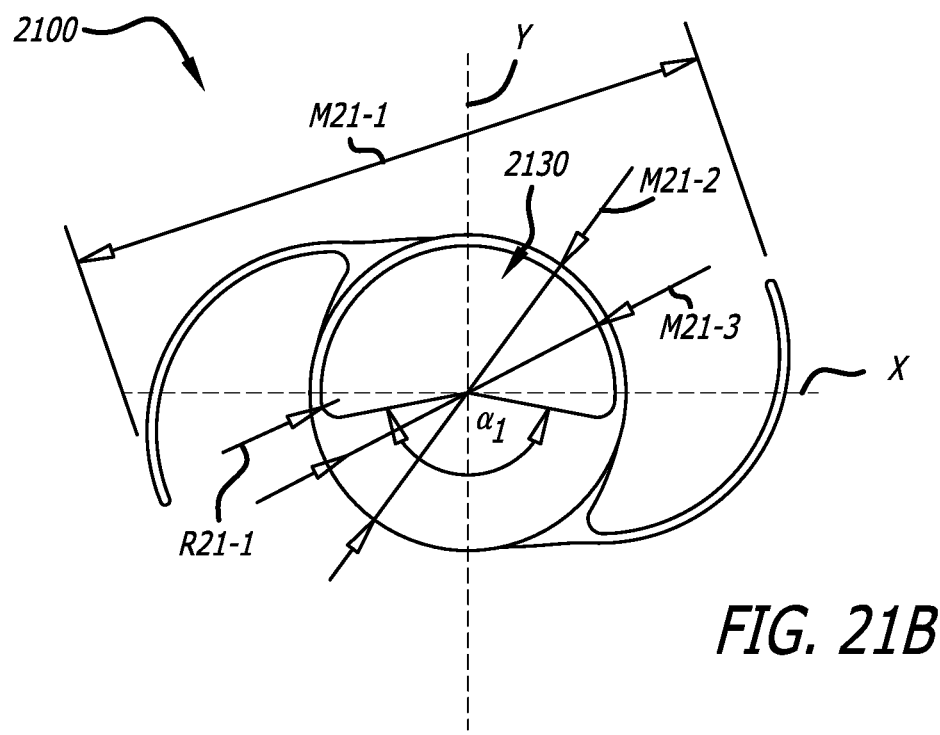
FIG. 21B depicts dimensions of the optical device of FIG. 21A.

FIGS. 21A and 21B show an example embodiment of an optical device 2100 including a partial or incomplete optic 2120, such as or similar to the partial or incomplete optic 200 of FIGS. 2A and 2B, and a circumferential ring 2102 and loop haptics 2150, such as or similar to those of the optical device 1100 of FIGS. 11A and 11B (the optical device 2100 and its partial or incomplete optic 2120, in various implementations, being of and embodying a lens/optic design that is configurable operatively to serve as or provide an add-on to an existing optical element or system). The circumferential ring 2102 includes an upper ring portion 2104 and a lower ring (/optic support) portion 2106 (e.g., shaped/configured as shown). The loop haptics 2150 include, at opposing exterior portions of the ring 2102, arms 2152 and base/interconnect elements 2160 (e.g., shaped/configured as shown). The upper ring portion 2104 includes an inner surface (denoted "$SCR_I$") and an outer surface (denoted "$SCR_O$"). The partial or incomplete optic 2120 includes or is provided with edge or side portions, e.g., two symmetrical surfaces (each denoted "SO"). The inner surface $SCR_I$ (of the upper ring portion 2104) together with the edge or side portion(s)/surface(s) SO (of the partial or incomplete optic 2120) define an opening 2130 (or an effectively optically irrelevant portion) of the partial or incomplete optic 2120. The partial or incomplete optic 2120 and the circumferential ring 2102 are made of a soft material (e.g., a foldable soft acrylic material such as described in US 2010/0145446, which is hereby incorporated by reference) (e.g., a soft acrylic material, such as is utilized in AF-1 6.0 mm buttons available from Hoya Surgical Optics), and the two curve-shaped arms 2152 (and their respective base/interconnect elements 2160) are made of a material that is harder (e.g., polymethylmethacrylate (PMMA)) than the material of the partial or incomplete optic 2120 and the circumferential ring 2102.

FIG. 21B depicts dimensions of the optical device 2100 as shown. By way of example, dimensions for the optical device 2100 can be as follows: angle α is approximately 160°; M21-1 is for example set at 12.5 mm; M21-2 is for example set at about 6.0 mm; and M21-3 is for example set at about 5.6 mm (the difference between M21-2 and M21-3 indicating the radial distance 0.2 mm between the inner and outer surfaces, $SCR_I$ and $SCR_O$, of the circumferential ring 2102).

The loop haptics 2150 (of the optical device 2100) include the base/interconnect elements 2160 shaped/configured and interconnected, as shown, at periphery portions of the upper ring portion 2104 (adjacent to the opening 2130) and the lower ring portion 2106 (adjacent to the partial or incomplete optic 2120), respectively.

With reference to FIGS. 21A and 21B, in an example method or process of installing (inserting) an optical device such as or similar to the optical device 2100 (e.g., into an incision made in a human eye), the lens is folded (or bent) along the x-axis (using tweezers or a lens case, for example).

Figure 22A:
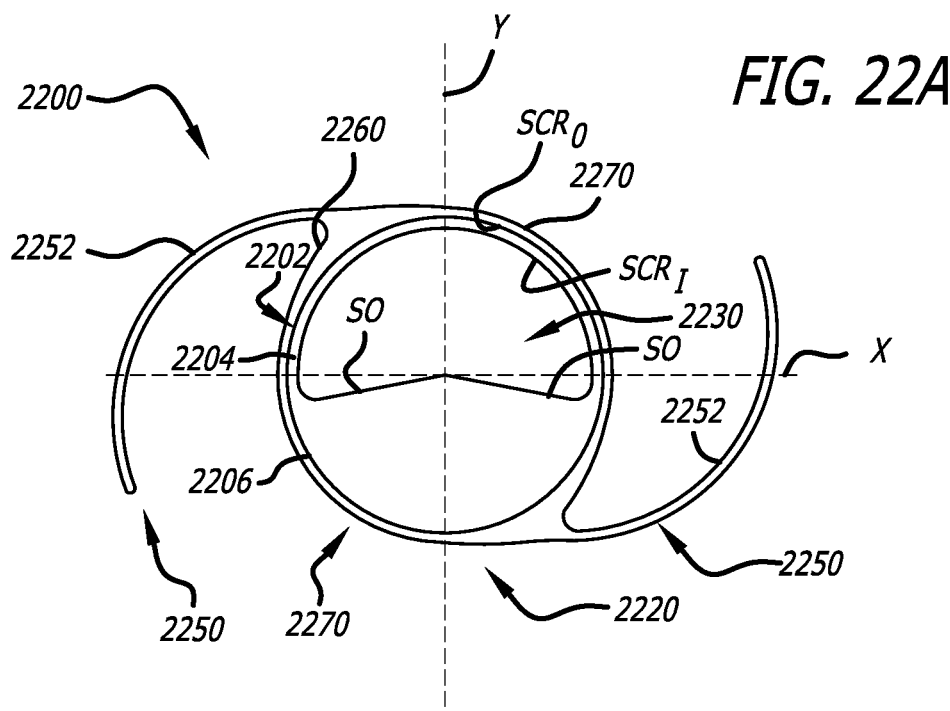
FIG. 22A is a plan view of an example embodiment of an optical device including a partial or incomplete optic, such as or similar to that of FIGS. 2A and 2B, and a circumferential ring and loop haptics having two curve-shaped arms (the optical device and its partial or incomplete optic, in various implementations, being of and embodying a lens/optic design that is configurable operatively to serve as or provide an add-on to an existing optical element or system), the loop haptics including, at opposing exterior portions of the circumferential ring, base/interconnect elements (of the two curve-shaped arms, respectively) and periphery support/interface structures, and the optical device being configured such that, the base/interconnect elements and the periphery support/interface structures, together, provide structural support at and about the entire periphery of the circumferential ring (of the optical device).
Figure 22B:
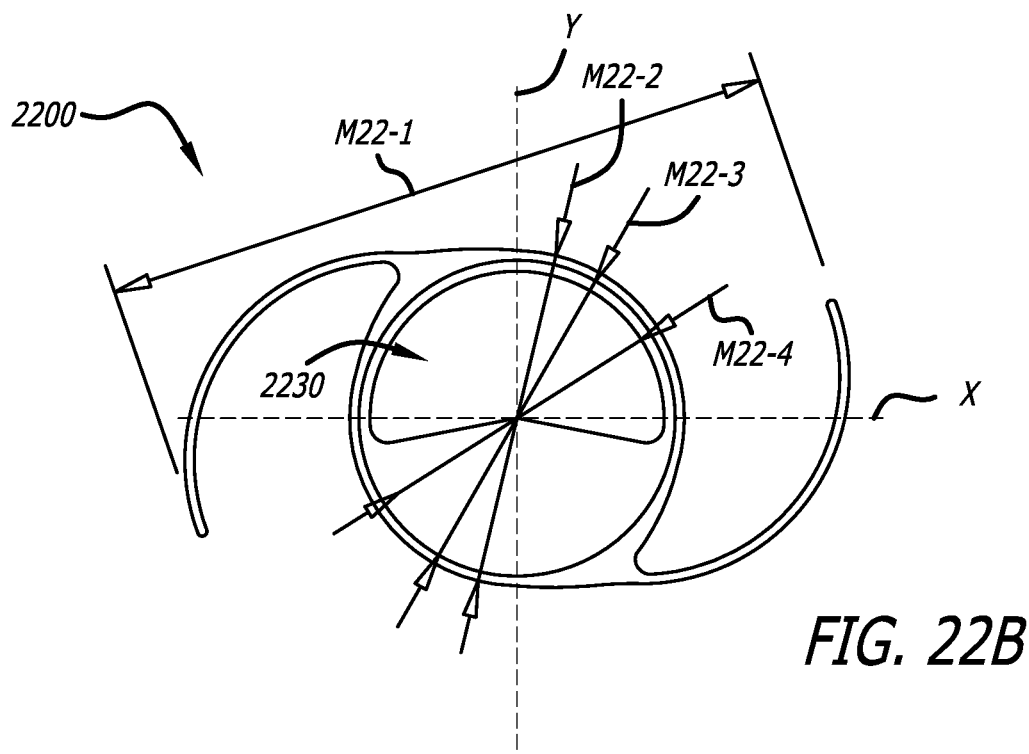
FIG. 22B depicts dimensions of the optical device of FIG. 22A.

FIGS. 22A and 22B show an example embodiment of an optical device 2200 including a partial or incomplete optic 2220, such as or similar to the partial or incomplete optic 200 of FIGS. 2A and 2B, and a circumferential ring 2202 and loop haptics 2250 (the optical device 2200 and its partial or incomplete optic 2220, in various implementations, being of and embodying a lens/optic design that is configurable operatively to serve as or provide an add-on to an existing optical element or system). The circumferential ring 2202 includes an upper ring portion 2204 and a lower ring (/optic support) portion 2206 (e.g., shaped/configured as shown). The loop haptics 2250 include, at opposing exterior portions of the ring 2202, arms 2252, base/interconnect elements 2260 (e.g., shaped/configured as shown) and (optical device) periphery support/interface structures 2270 (e.g., integrally formed with the base/interconnect elements 2260 as shown). In this example design of an optical device, together, the base/interconnect elements 2260 and the periphery support/interface structures 2270 provide structural support at and about the entire periphery of the optical device 2200. The upper ring portion 2204 includes an inner surface (denoted "$SCR_I$") and an outer surface (denoted "$SCR_O$"). The partial or incomplete optic 2220 includes or is provided with edge or side portions, e.g., two symmetrical surfaces (each denoted "SO"). The inner surface $SCR_I$ (of the upper ring portion 2204) together with the edge or side portion(s)/surface(s) SO (of the partial or incomplete optic 2220) define an opening 2230 (or an effectively optically irrelevant portion) of the partial or incomplete optic 2220.

The partial or incomplete optic 2220 and the circumferential ring 2202 are made of a soft material (e.g., a foldable soft acrylic material such as described in US 2010/0145446, which is hereby incorporated by reference) (e.g., a soft acrylic material, such as is utilized in AF-1 6.0 mm buttons available from Hoya Surgical Optics), and the two curve-shaped arms 2252 (and their respective base/interconnect elements 2260) and the (optical device) periphery support/interface structures 2270 are made of a material that is harder (e.g., polymethylmethacrylate (PMMA)) than the material of the partial or incomplete optic 2220 and the circumferential ring 2202.

FIG. 22B depicts dimensions of the optical device 2200 as shown. By way of example, dimensions for the optical device 2200 can be as follows: M22-1 is for example set at 13.0 mm; M22-2 is for example set at about 6.5 mm; M22-3 is for example set at about 6.2 mm (the difference between M22-2 and M22-3 indicating the radial distance between inner and outer surfaces as shown of the (optical device) periphery support/interface structures 2270); and M22-4 is for example set at about 5.6 mm (the difference between M22-3 and M22-4 indicating the radial distance between the inner and outer surfaces, $SCR_I$ and $SCR_O$, of the circumferential ring 2202).

The loop haptics 2250 (of the optical device 2200) include the base/interconnect elements 2260 shaped/configured and interconnected, as shown, at periphery portions of the upper ring portion 2104 (adjacent to the opening 2130) and the lower ring portion 2106 (adjacent to the partial or incomplete optic 2120), respectively, the base/interconnect elements 2260 and the periphery support/interface structures 2270 being configured (e.g., as shown) to provide structural support at and about the entire periphery of the circumferential ring 2202 (of the optical device 2200).

With reference to FIGS. 22A and 22B, in an example method or process of installing (inserting) an optical device such as or similar to the optical device 2200 (e.g., into an incision made in a human eye), the two curve-shaped arms 2252 are positioned close to the periphery of the lens (e.g., adjacent to the periphery support/interface structures 2270), however, the lens is not folded (or bent) requiring a larger incision size (e.g., at least 6.5 mm for installing/inserting the example optical device of FIGS. 22A and 22B). This could be suitable for complicated eye cases such as sulcus fixation or sclera suturing for patients with AMD (not necessarily cataract-based), or cases where PMMA IOLs are suitable.

Thus, in an example embodiment, an optical device includes a partial or incomplete optic configured operatively as an add-on (e.g., supplemental lens/optic) for an (existing) optical element or system, the partial or incomplete optic having an active area (or portion(s), e.g., one or more regions or sectors) configured in relation to the optical element or system such that the partial or incomplete optic controls or changes foci of light incident upon or provided to the active area, but does not control or change foci of light bypassing optically relevant portions of the partial or incomplete optic; wherein the optical device includes an opening adjacent to and/or not overlapping the active area, the partial or incomplete optic includes a circumferential ring that defines a portion of the opening, and the optical device further includes: a haptic or support secured to and configured to provide structural support at and about an entire periphery of the circumferential ring to prevent bending of the circumferential ring adjacent to the opening (which otherwise/if not so prevented or at least mitigated would result in the optical device having a greater decentration and a greater optical tilt) when arms of the haptic or support are compressed. In example embodiments and implementations, the partial or incomplete optic and the circumferential ring are made of a first material (e.g., a soft acrylic material), and the haptic or support includes one or more periphery support/interface structures made of a second material that is harder (e.g., polymethylmethacrylate (PMMA)) than the first material.

Figure 23A:
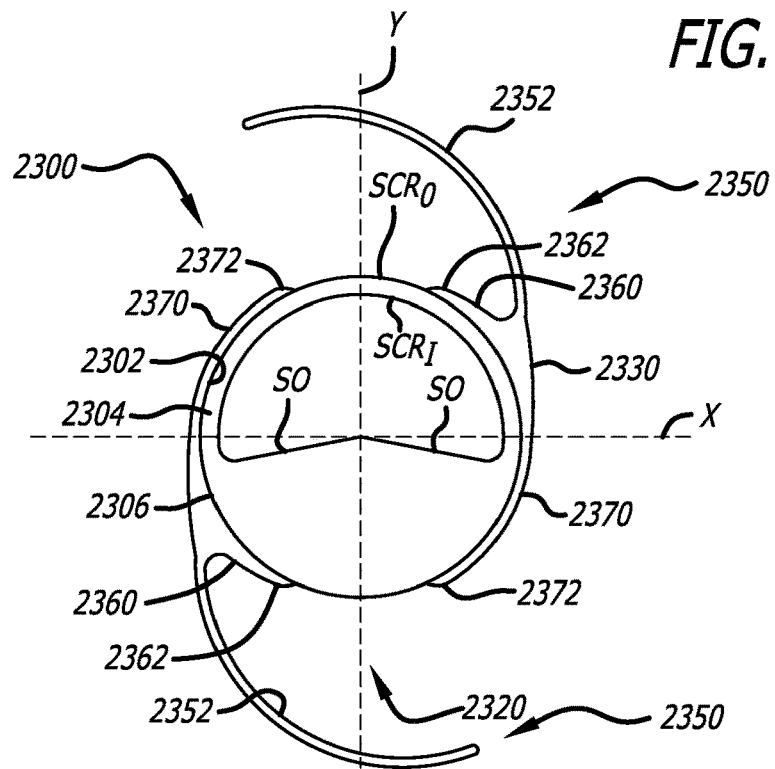
FIG. 23A is a plan view of an example embodiment of an optical device including a partial or incomplete optic, such as or similar to that of FIGS. 2A and 2B, and a circumferential ring and loop haptics having two curve-shaped arms (the optical device and its partial or incomplete optic, in various implementations, being of and embodying a lens/optic design that is configurable operatively to serve as or provide an add-on to an existing optical element or system), the loop haptics including, at opposing exterior portions of the circumferential ring, base/interconnect elements (of the two curve-shaped arms, respectively) and periphery support/interface structures which are made of a material that is harder (less flexible) than the material(s) of the partial or incomplete optic and the circumferential ring, and the optical device being configured such that, the base/interconnect elements and the periphery support/interface structures, together (and symmetrically or otherwise configured in relation to one or more boundaries of the partial or incomplete optic), provide structural support at periphery portions of the circumferential ring (of the optical device)
Figure 23B:
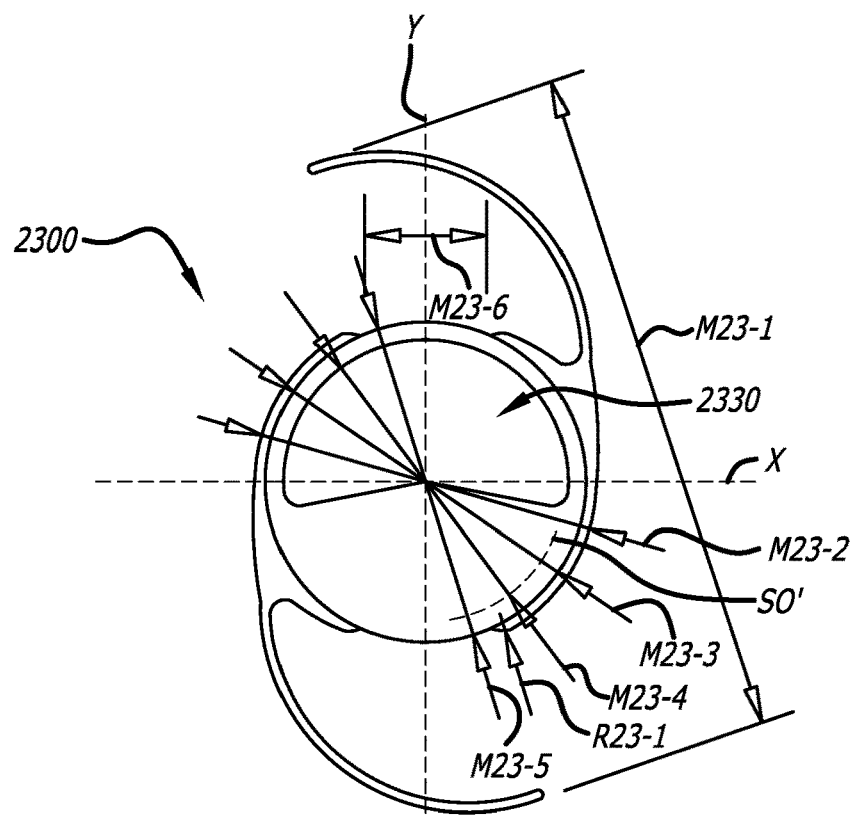
FIG. 23B depicts dimensions of the optical device of FIG. 23A.

FIGS. 23A and 23B show an example embodiment of an optical device 2300 including a partial or incomplete optic 2320, such as or similar to the partial or incomplete optic 200 of FIGS. 2A and 2B, and a circumferential ring 2302 and loop haptics 2350 (the optical device 2300 and its partial or incomplete optic 2320, in various implementations, being of and embodying a lens/optic design that is configurable operatively to serve as or provide an add-on to an existing optical element or system). The circumferential ring 2302 includes an upper ring portion 2304 and a lower ring (/optic support) portion 2306 (e.g., shaped/configured as shown). The loop haptics 2350 include, (periphery support/interface structures) at opposing exterior portions of the ring 2302, arms 2352, base/interconnect elements 2360 (including curved end portions 2362, e.g., shaped/configured as shown) and (optical device) periphery support/interface structures 2370 (e.g., integrally formed with the base/interconnect elements 2360 and/or including curved end portions 2372—shaped/configured as shown). In this example design of an optical device, together, the base/interconnect elements 2360 and the periphery support/interface structures 2370 provide structural support at and about the periphery portions of the optical device 2300 (e.g., as shown). The upper ring portion 2304 includes an inner surface (denoted "$SCR_I$") and an outer surface (denoted "$SCR_O$"). The partial or incomplete optic 2320 includes or is provided with edge or side portions, e.g., two symmetrical surfaces (each denoted "SO") and an adjoining curved side portion (denoted "SO'"). In at least one example embodiment, an (optical) active area (or an optically relevant portion) of the partial or incomplete optic 2320 has a (peripheral) boundary which, at least in part, includes or is defined by one or more edge or side portions/surfaces of the optic 2320 (such as for example the surfaces/portions SO, SO'). The inner surface $SCR_I$ (of the upper ring portion 2304) together with the edge or side portion(s)/surface(s) SO (of the partial or incomplete optic 2320) define an opening 2330 (or an effectively optically irrelevant portion) of the partial or incomplete optic 2320.

The partial or incomplete optic 2320 and the circumferential ring 2302 are made of a soft material (e.g., a foldable soft acrylic material such as described in US 2010/0145446, which is hereby incorporated by reference) (e.g., a soft acrylic material, such as is utilized in AF-1 6.0 mm buttons available from Hoya Surgical Optics), and the two curve-shaped arms 2352, and their respective base/interconnect elements 2360 (and curved end portions 2362 thereof), and the (optical device) periphery support/interface structures 2370 (and curved end portions 2372 thereof) are made of a material that is harder (e.g., polymethylmethacrylate (PMMA)) than the material of the partial or incomplete optic 2320 and the circumferential ring 2302.

FIG. 23B depicts dimensions of the optical device 2300 as shown. By way of example, dimensions for the optical device 2300 can be as follows: M23-1 is for example set at 13.0 mm; M23-2 is for example set at about 6.5 mm; M23-3 is for example set at about 6.2 mm (the difference between M23-2 and M23-3 indicating the radial distance between inner and outer surfaces as shown of the (optical device) periphery support/interface structures 2370); M23-4 is for example set at about 5.6 mm (the difference between M23-3 and M23-4 indicating the radial distance between the inner (/lens interface) surface of the (optical device) periphery support/interface structure 2370 and the outer periphery of the active area of the partial or incomplete optic 2320); M23-5 is for example set at about 6.1 mm; M23-6 is for example set at about 2.55 mm (M23-6 indicating the distance, orthogonally in relation to the y-axis, between the curved end portions 2362 and 2372 of the respective periphery support/interface structures—FIGS. 23A and 23B, M23-6 additionally representing boundaries of other periphery portions of the circumferential ring (at opposing sides of the circumferential ring and equidistant about the y-axis, in this example) that are not directly connected/interfaced to either of the periphery support/interface structures, the optical device being foldable at/through the other periphery portions (and, in this example, along the y-axis) (e.g., during a process of installing/inserting the optical device into an incision)); and M23-1 in relation to the curved end portions 2362 and 2372 is set for example at about R0.3.

The loop haptics 2350 (of the optical device 2300) include the base/interconnect elements 2360 and the periphery support/interface structures 2370 shaped/configured and interconnected, as shown (e.g., symmetrically in relation to the opening 2330 and/or one or more boundaries of the partial or incomplete optic 2320) (e.g., symmetrically in relation to the y-axis), at periphery portions of the upper ring portion 2304 (adjacent to the opening 2330) and the lower ring portion 2306 (adjacent to the partial or incomplete optic 2320), and the optical device 2300 being configured (e.g., as shown) such that, the base/interconnect elements 2360 and the periphery support/interface structures 2370, together (e.g., symmetrically in relation to one or more boundaries of the partial or incomplete optic 2320), provide structural support at periphery portions of the circumferential ring 2302 (of the optical device 2300).

With reference to FIGS. 23A and 23B, in an example method or process of installing (inserting) an optical device such as or similar to the optical device 2300 (e.g., into an incision made in a human eye), the lens is folded (or bent) along the y-axis (using tweezers or a lens case, for example). Thus, the example optical device of FIGS. 23A and 23B is both foldable and configured to provide structural support at periphery portions of the circumferential ring to prevent bending of the circumferential ring (which otherwise/if not so prevented or at least mitigated would result in the optical device having a greater decentration and a greater optical tilt) when arms of the haptic or support are compressed. If a 5.5 mm button is utilized (produced), optical devices such or similar to the example optical device 2200 (FIGS. 22A and 22B) or such or similar to the example optical device 2300 (FIGS. 23A and 23B) can produce 6.0 mm of optical diameter.

Thus, in an example embodiment, an optical device includes a partial or incomplete optic configured operatively as an add-on (e.g., supplemental lens/optic) for an (existing) optical element or system, the partial or incomplete optic having an active area (or portion(s), e.g., one or more regions or sectors) configured in relation to the optical element or system such that the partial or incomplete optic controls or changes foci of light incident upon or provided to the active area, but does not control or change foci of light bypassing optically relevant portions of the partial or incomplete optic; wherein the optical device includes an opening adjacent to and/or not overlapping the active area, the partial or incomplete optic includes a circumferential ring that defines a portion of the opening, and the optical device further includes: a haptic or support secured to and configured to provide structural support at periphery portions of the circumferential ring to prevent bending of the circumferential ring (which otherwise/if not so prevented or at least mitigated would result in the optical device having a greater decentration and a greater optical tilt) when arms of the haptic or support are compressed. In example embodiments and implementations, the partial or incomplete optic and the circumferential ring are made of a first material (e.g., a soft acrylic material), and the haptic or support includes (one or more) periphery support/interface structures made of a second material that is harder (e.g., polymethylmethacrylate (PMMA)) than the first material. In example embodiments and implementations, the haptic or support includes periphery support/interface structures that are symmetrically (and/or non-symmetrically) configured in relation to one or more boundaries of the partial or incomplete optic. In example embodiments and implementations, the haptic or support includes periphery support/interface structures that are symmetrically configured in relation to the opening, non-symmetrically configured in relation to the opening, or a combination thereof. In example embodiments and implementations, the haptic or support includes periphery support/interface structures that are not directly connected to other periphery portions (e.g., at opposing sides) of the circumferential ring and configured such that the optical device is foldable at (e.g., along an axis traversing) said other periphery portions (e.g., during a process of installing/inserting the optical device into an incision). In example embodiments and implementations, the haptic or support includes periphery support/interface structures that are configured at opposite sides of the optical device (either symmetrically or non-symmetrically) in relation to portions of the optical device at which the optical device is foldable. In example embodiments and implementations, the periphery portions are at opposing sides of the circumferential ring and approximately equidistant from an axis (e.g., defined in relation to the partial or incomplete optic and/or the opening) intersecting portions of the optical device at which the optical device is foldable. In example embodiments and implementations, the haptic or support includes periphery support/interface structures with curved end portions, and the circumferential ring includes exposed periphery portions adjacent to the curved end portions. In example embodiments and implementations, the periphery portions of the circumferential ring are smooth/uniform in their curvature at the exposed periphery portions (and about the entire circumference of the lens), and the curved end portions 2362 and 2372 taper off (semi-gradually) to the exposed lens material (e.g., curving/transitioning as shown/described herein toward the exposed periphery portions of the circumferential ring).

Although the present invention(s) has(have) been described in terms of the example embodiments above, numerous modifications and/or additions to the above-described embodiments would be readily apparent to one skilled in the art. It is intended that the scope of the present invention(s) extend to all such modifications and/or additions.

What is claimed is:

1. A method for enhancing vision, the method comprising:
    adding a partial or incomplete optic as an add-on to an existing optical system that has a line of sight, the partial or incomplete optic having a fan-shaped optically active area configured in relation to the existing optical system such that the line of sight passes through the fan-shaped optically active area and the partial or incomplete optic controls or changes foci of light incident upon or provided to the fan-shaped optically active area, but does not control or change foci of light bypassing optically relevant portions of the partial or incomplete optic,
    wherein the existing optical system includes an intraocular lens (IOL) implanted in an eye of a patient, and the step of adding a partial or incomplete optic is performed subsequently to the intraocular lens being implanted in the eye of the patient, and
    wherein the partial or incomplete optic is devoid of haptics.

2. The method for enhancing vision of claim 1, wherein the step of adding a partial or incomplete optic includes positioning the partial or incomplete optic in relation to the existing optical system such that the active area controls or changes foci of light incident upon or provided to the existing optical system at the active area.

3. The method for enhancing vision of claim 1, wherein the step of adding a partial or incomplete optic includes
    positioning the partial or incomplete optic in the eye at a location, the location being:
    in front of an iris/within an anterior chamber,
    at or near an iris,
    behind an iris/in sulcus, or
    inside a capsular bag.

4. The method for enhancing vision of claim 1, wherein the step of adding a partial or incomplete optic includes
    utilizing one or more portions of the eye to secure the partial or incomplete optic within the eye, the portion(s) of the eye including one or more of:
    an iris,
    an anterior chamber,
    a sulcus, and
    a capsular bag.

5. The method for enhancing vision of claim 1, wherein the active area includes edge or side portions that block or diffuse light.

6. The method for enhancing vision of claim 5, wherein the edge or side portions that block or diffuse light include a surface treatment or finish at the edge or side portions from outside-in without affecting optical areas.

7. The method for enhancing vision of claim 5, wherein the edge or side portions that block or diffuse light include a light absorbing surface layer.

8. The method for enhancing vision of claim 5, wherein the edge or side portions that block or diffuse light have a gloss unit (GU) value that is less than 30.

9. The method for enhancing vision of claim 5, wherein the edge or side portions that block or diffuse light have a surface roughness with peak-valley height values of 7-15 microns.

10. The method for enhancing vision of claim 5, wherein the edge or side portions that block or diffuse light are produced utilizing one or more of:
    a lithography technique,
    an etching technique, and
    an UV/Ozone surface technique,
    to apply and/or modify one or more surface structures at the edge or side portions.

11. The method for enhancing vision of claim 5, wherein the edge or side portions that block or diffuse light include nano-structures that have nano-tips or cones.

12. The method for enhancing vision of claim 5, wherein the edge or side portions that block or diffuse light include nano-structures that are cone-shaped or approximately cone-shaped, the nano-structures being 100-300 nm in base diameter and 1000-16000 nm in height.

13. The method for enhancing vision of claim 5, wherein the edge or side portions that block or diffuse light include nano-structures at the edge or side portions, the nano-structures including: nano-tips, nano-arrays, aperiodic or other arrays of nano-structures, antireflection structures, biomimetic structures, or a combination or combinations thereof.

* * * * *